United States Patent
Ben-Haim et al.

(10) Patent No.: US 11,471,067 B2
(45) Date of Patent: Oct. 18, 2022

(54) INTRABODY PROBE NAVIGATION BY ELECTRICAL SELF-SENSING

(71) Applicant: Navix International Limited, Road Town (VG)

(72) Inventors: Shlomo Ben-Haim, Milan (IT); Zalman Ibragimov, Rehovot (IL); Yehonatan Ben David, Tel-Aviv (IL)

(73) Assignee: Navix International Limited, Road Town (VG)

( * ) Notice: Subject to any disclaimer, the term of this patent is extended or adjusted under 35 U.S.C. 154(b) by 477 days.

(21) Appl. No.: 16/484,501

(22) PCT Filed: Feb. 8, 2018

(86) PCT No.: PCT/IB2018/050784
§ 371 (c)(1),
(2) Date: Aug. 8, 2019

(87) PCT Pub. No.: WO2018/146613
PCT Pub. Date: Aug. 16, 2018

(65) Prior Publication Data
US 2020/0000368 A1    Jan. 2, 2020

Related U.S. Application Data

(63) Continuation-in-part of application No. PCT/IB2018/050192, filed on Jan. 12, 2018.
(Continued)

(51) Int. Cl.
*A61B 5/06* (2006.01)
*A61B 5/0538* (2021.01)
(Continued)

(52) U.S. Cl.
CPC ............ *A61B 5/065* (2013.01); *A61B 5/0538* (2013.01); *A61B 5/285* (2021.01); *A61B 5/287* (2021.01); *A61B 5/4233* (2013.01); *A61B 5/6852* (2013.01)

(58) Field of Classification Search
None
See application file for complete search history.

(56) References Cited

U.S. PATENT DOCUMENTS

| | | |
|---|---|---|
| 5,465,730 A | 11/1995 | Zadehkoochak et al. |
| 5,553,611 A | 9/1996 | Budd et al. |

(Continued)

FOREIGN PATENT DOCUMENTS

| | | |
|---|---|---|
| CN | 102056537 | 5/2011 |
| CN | 103687533 | 3/2014 |

(Continued)

OTHER PUBLICATIONS

International Preliminary Report on Patentability dated Aug. 22, 2019 From the International Bureau of WIPO Re. Application No. PCT/IB2018/050784. (11 Pages).

(Continued)

*Primary Examiner* — Yi-Shan Yang

(57) ABSTRACT

Methods and systems for position determination are described for using an intrabody probe having a plurality of electrodes to generate a plurality of different electrical fields, and to also measure, using the plurality of electrodes, a measurement set (a $V_{e-e}$ measurement set) comprising a plurality of measurements of the plurality of different electrical fields while the probe remains in one position. From the $V_{e-e}$ measurement set, spatial position coordinates for the intrabody probe are estimated within an intrabody coordinate system, using an established mapping between previously observed $V_{e-e}$ measurement sets and positions in the (Continued)

intrabody coordinate system. Systems and methods for generating and selecting such mappings are also described.

34 Claims, 7 Drawing Sheets

Related U.S. Application Data

(60) Provisional application No. 62/456,752, filed on Feb. 9, 2017, provisional application No. 62/546,775, filed on Aug. 17, 2017, provisional application No. 62/445,433, filed on Jan. 12, 2017.

(51) Int. Cl.
*A61B 5/285* (2021.01)
*A61B 5/00* (2006.01)
*A61B 5/287* (2021.01)

(56) References Cited

U.S. PATENT DOCUMENTS

| | | |
|---|---|---|
| 5,662,108 A | 9/1997 | Budd et al. |
| 5,697,377 A | 12/1997 | Wittkampf |
| 6,240,307 B1 | 5/2001 | Beatty et al. |
| 6,640,119 B1 | 10/2003 | Budd et al. |
| 6,728,562 B1 | 4/2004 | Budd et al. |
| 6,826,420 B1 | 11/2004 | Beatty et al. |
| 6,939,309 B1 | 9/2005 | Beatty et al. |
| 6,947,785 B1 | 9/2005 | Beatty et al. |
| 6,978,168 B2 | 12/2005 | Beatty et al. |
| 6,990,370 B1 | 1/2006 | Beatty et al. |
| 7,187,973 B2 | 3/2007 | Hauck |
| 7,189,208 B1 | 3/2007 | Beatty et al. |
| 7,996,060 B2 | 8/2011 | Trofimov et al. |
| 2003/0018251 A1 | 1/2003 | Solomon |
| 2003/0078494 A1 | 4/2003 | Panescu et al. |
| 2004/0254437 A1 | 12/2004 | Hauck et al. |
| 2007/0049817 A1 | 3/2007 | Preiss et al. |
| 2007/0299351 A1 | 12/2007 | Harlev et al. |
| 2007/0299352 A1* | 12/2007 | Harlev ............... A61B 5/6852 600/509 |
| 2008/0190438 A1* | 8/2008 | Harlev .................. A61B 90/36 128/898 |
| 2009/0076483 A1 | 3/2009 | Danehorn |
| 2009/0171274 A1 | 7/2009 | Harlev et al. |
| 2009/0262109 A1 | 10/2009 | Markowitz et al. |
| 2009/0264778 A1 | 10/2009 | Markowitz et al. |
| 2012/0059249 A1 | 3/2012 | Verard et al. |
| 2012/0150046 A1 | 6/2012 | Watson et al. |
| 2014/0275991 A1 | 9/2014 | Potter et al. |
| 2016/0045133 A1 | 2/2016 | Balachandran et al. |
| 2016/0061599 A1 | 3/2016 | Zeng et al. |
| 2016/0242667 A1 | 8/2016 | Fay et al. |
| 2019/0336035 A1 | 11/2019 | Dichterman et al. |
| 2020/0085504 A1 | 3/2020 | Schwartz et al. |
| 2020/0289025 A1 | 9/2020 | Dichterman et al. |
| 2021/0128009 A1 | 5/2021 | Ben-Haim |

FOREIGN PATENT DOCUMENTS

| | | |
|---|---|---|
| CN | 105377135 | 6/2022 |
| EP | 0974936 | 1/2000 |
| EP | 1767166 | 3/2007 |
| JP | 2003/527164 | 9/2003 |
| WO | WO 98/01069 | 1/1998 |
| WO | WO 2006/055286 | 5/2006 |
| WO | WO 2008/097767 | 8/2008 |
| WO | WO 2010/129095 | 11/2010 |
| WO | WO 2011/142931 | 11/2011 |
| WO | WO 2012/092016 | 7/2012 |
| WO | WO2014/036439 | 3/2014 |
| WO | WO 2014/118535 | 8/2014 |
| WO | WO 2014/182822 | 11/2014 |
| WO | WO 2016/033599 | 3/2016 |
| WO | WO 2018/078540 | 5/2018 |
| WO | WO 2018/130974 | 7/2018 |
| WO | WO 2018/146613 | 8/2018 |
| WO | WO 2018/146613 A2 | 8/2018 |
| WO | WO 2019/034944 | 2/2019 |

OTHER PUBLICATIONS

International Preliminary Report on Patentability dated Jul. 25, 2019 From the International Bureau of WIPO Re. Application No. PCT/IB2018/050192. (8 Pages).
International Search Report and the Written Opinion dated May 9, 2018 From the International Searching Authority Re. Application No. PCT/IB2018/050192. (16 Pages).
International Search Report and the Written Opinion dated Sep. 25, 2018 From the International Searching Authority Re. Application No. PCT/IB2018/050784. (18 Pages).
International Search Report and the Written Opinion dated Nov. 30, 2018 From the International Searching Authority Re. Application No. PCT/IB2018/055344. (15 Pages).
Invitation to Pay Additional Fees, Communication Relating to the Results of the Partial International Search and the Provisional Opinion dated Jun. 26, 2018 From the International Searching Authority Re. Application No. PCT/IB2018/050784. (13 Pages).
Boston Scientific "Rhythmia™ Mapping System: Rhythmia Disposables Product Information: Intellamap Orion™ High Resolution Mapping Catheter", Boston Scientific, 2 P., Sep. 2015.
Notification Regarding Third-Party Preissuance Submission dated Jan. 29, 2021 From the US Patent and Trademark Office Re. U.S. Appl. No. 16/338,710.(2 Pages).
Third Party IDS Submission under 37 CFR 1.290 filed on Jan. 14, 2021 From the US Patent and Trademark Office Re. U.S. Appl. No. 16/338,710.(2 Pages).
International Preliminary Report on Patentability dated Feb. 27, 2020 From the International Bureau of WIPO Re. Application No. PCT/IB2018/055344. (8 Pages).
International Preliminary Report on Patentability dated Feb. 27, 2020 From the International Bureau of WIPO Re. Application No. PCT/IB2018/056158. (8 Pages).
Official Action dated Jun. 4, 2021 from the US Patent and Trademark Office Re. U.S. Appl. No. 16/338,710. (22 pages).
Official Action dated May 5, 2021 from the US Patent and Trademark Office Re. U.S. Appl. No. 16/476,875. (35 pages).
International Preliminary Report on Patentability dated May 9, 2019 From the International Bureau of WIPO Re. Application No. PCT/IB2017/056616. (8 Pages).
International Search Report and the Written Opinion dated Feb. 1, 2018 From the International Searching Authority Re. Application No. PCT/IB2017/056616. (14 Pages).
Crospon "Esophageal Treatment by Esoflip®", Crospon, Product Sheet, 4 P., 2017.
Crospon "Flip® Technology", Crospon, Product Sheet, 6 P., 2017.
Myronenko et al. "Non-Rigid Point Set Registration: Coherent Point Drift", Advances in Neural Information Processing Systems, NIPS, 19: 1009-1016, 2009.
Notification of Office Action and Search Report dated Jan. 11, 2022 From the State Intellectual Property Office of the People's Republic of China Re. Application No. 201880022135.4. (8 Pages).

* cited by examiner

INTRABODY PROBE NAVIGATION BY ELECTRICAL SELF-SENSING

RELATED APPLICATIONS

This application is a National Phase of PCT Patent Application No. PCT/IB2018/050784 having International filing date of Feb. 8, 2018, which claims the benefit of priority under 35 USC § 119(e) of U.S. Provisional Patent Application No. 62/456,752 filed on Feb. 9, 2017 and PCT Patent Application No. PCT/IB2018/050192 having the International filing date of Jan. 12, 2018.

PCT Patent Application No. PCT/IB2018/050784 is also a CIP of PCT Patent Application No. PCT/IB2018/050192 having the International filing date of Jan. 12, 2018 which claims the benefit of priority under 35 USC § 119(e) of U.S. Provisional Patent Application Nos. 62/546,775, filed on Aug. 17, 2017 and 62/445,433, filed on Jan. 12, 2017.

The contents of the above applications are all incorporated by reference as if fully set forth herein in their entirety.

FIELD AND BACKGROUND OF THE INVENTION

The present invention, in some embodiments thereof, relates to the field of navigation of body cavities by intrabody probes, and more particularly, to determination of intra-body probe position, for example during navigation of body cavities.

Several medical procedures in cardiology and other medical fields comprise the use of intrabody probes such as catheter probes to reach tissue targeted for diagnosis and/or treatment while minimizing procedure invasiveness. Early imaging-based techniques (such as fluoroscopy) for navigation of the catheter and monitoring of treatments continue to be refined, and are now joined by techniques such as electrical field-guided position sensing systems.

SUMMARY OF THE INVENTION

There is provided, in accordance with some embodiments of the present disclosure, a method of estimating an intrabody position of a probe having a plurality of electrodes, the method comprising: generating a plurality of electrical fields using the plurality of electrodes; measuring, at the intrabody position and using the plurality of electrodes, a position-identifying data set comprising a plurality of measurements of the plurality of electrical fields; and estimating position coordinates for the intrabody position based on the position-identifying data set.

There is provided, in accordance with some embodiments of the present disclosure, a method of estimating an intrabody position of a probe having a plurality of electrodes, the method comprising: generating, from the intrabody position, a plurality of electrical fields using the plurality of electrodes; measuring, at the intrabody position and also using the plurality of electrodes, a position-identifying data set comprising a plurality of measurements of the plurality of electrical fields; and estimating a plurality of position coordinates defining the intrabody position within a spatial coordinate system, based on the position-identifying data set.

In some embodiments, measurements of the position-identifying data set measured by the plurality of electrodes differ at different positions of the probe, due to interactions of electrical fields generated by the plurality of electrodes with the different electrical environment of different intrabody positions.

In some embodiments, the estimating comprises determining the position coordinates based on a mapping between position coordinates and position-identifying data sets.

In some embodiments, the measuring detects differences among position-identifying data sets measured by the plurality of electrodes at different intrabody positions due to changes in isopotential surface shapes of the plurality of electrical fields as the probe moves.

In some embodiments, the measuring detects differences among position-identifying data sets measured by the plurality of electrodes at different intrabody positions due to changes, as the probe moves, in measured values of voltages established by controlled electrical currents.

In some embodiments, the position coordinates correspond to coordinates in a physical spatial coordinate system.

In some embodiments, the mapping is between position coordinates defined by anatomical data and position-identifying data sets.

In some embodiments, the anatomical data comprise anatomical imaging data of a subject in which the probe is positioned.

In some embodiments, the mapping uses position coordinates defined with respect to measurements of crossing intrabody electrical fields generated by electrodes positioned away from the probe.

In some embodiments, the crossing intrabody electrical fields are generated from body surface electrodes.

In some embodiments, the plurality of electrical fields comprises electrical fields generated at a plurality of frequencies.

In some embodiments, the frequencies of the plurality of frequencies are separated from each other in steps of at least about 100 Hz.

In some embodiments, the plurality of electrical fields are generated simultaneously.

In some embodiments, the plurality of electrical fields is generated from at least two of the plurality of electrodes.

In some embodiments, the plurality of electrical fields is generated from at least four of the plurality of electrodes.

In some embodiments, the plurality of electrical fields is measured by at least two of the plurality of electrodes.

In some embodiments, the plurality of electrical fields is measured by at least four of the plurality of electrodes.

In some embodiments, the plurality of electrical fields comprises at least 4 electrical fields, each measured from two or more of the plurality of electrodes.

In some embodiments, the plurality of electrical fields comprises at least 16 electrical fields, each measured from four or more of the plurality of electrodes.

In some embodiments, the method comprises using the estimated position coordinates to guide navigation of the probe within a body cavity.

In some embodiments, the method comprises using the estimated position coordinates in reconstructing a shape of a body cavity.

There is provided, in accordance with some embodiments of the present disclosure, a method of mapping a body cavity of a subject for navigation by a probe having a plurality of electrodes, the method comprising: receiving from the plurality of electrodes a position-identifying data set from each of a plurality of positions of the probe within the body cavity, the position-identifying data set comprising measurements, made by the plurality of electrodes, of a plurality of electrical fields, each generated by one of the plurality of electrodes; associating each position-identifying data set to the intrabody position at which it is measured to form a mapping; and storing the mapping for use in navigation of a probe.

There is provided, in accordance with some embodiments of the present disclosure, a system for use in intrabody navigation of a probe having a plurality of electrodes, comprising a processor configured to: receive from the plurality of electrodes a position-identifying data set from each of a plurality of positions of the probe within the body cavity, the position-identifying data set comprising measurements, made by the plurality of electrodes, of a plurality of electrical fields, each generated by one of the plurality of electrodes; and estimate position coordinates for the probe within a coordinate system, based on the position-identifying data set.

In some embodiments, the processor is configured to estimate the intrabody position based on a mapping between intrabody positions and position-identifying data sets.

There is provided, in accordance with some embodiments of the present disclosure, a method of estimating an intrabody position of a probe comprising a radio frequency-receiving electrode and positioned in a body cavity of a subject, the method comprising: analyzing measurements of radio frequency signals received by the radio frequency-receiving electrode from a radio frequency-transmitting electrode that transmits radio frequency signals from within the body of the subject; and estimating the intrabody position of the probe with respect to the body cavity based on results of the analyzing.

In some embodiments, the radio frequency-receiving electrode receives the radio frequency signals when the radio frequency-receiving electrode is in a heart chamber of the subject.

In some embodiments, the radio frequency-transmitting electrode transmits the radio frequency signals from within the heart chamber.

In some embodiments, the radio frequency-receiving electrode and the radio frequency-transmitting electrode are parts of the probe.

In some embodiments, the radio frequency-receiving electrode and the radio frequency-transmitting electrode are the same.

In some embodiments, the radio frequency-transmitting electrode transmits the radio frequency signals from within the coronary sinus of the heart of the subject.

In some embodiments, the analyzing comprises analyzing measurements of radio frequency signals received by a plurality of radio frequency-receiving electrodes, all forming parts of the probe; and the estimating comprises estimating the intrabody position of the probe with respect to the body cavity based on results of the analyzing.

In some embodiments, the analyzing comprises analyzing measurements of radio frequency signals received by radio frequency-receiving electrodes from a plurality of radio frequency-transmitting electrodes, each transmitting radio frequency signals at a respective frequency.

In some embodiments, the analyzing comprises transforming the measurements to be analyzed using a transformation generated before the measurements to be analyzed were measured.

In some embodiments, the analyzing comprises: selecting a transformation from among a plurality of transformations generated before the measurements to be analyzed were measured; and transforming the measurements to be analyzed using the selected transformation.

In some embodiments, each of the plurality of transformations is constructed using a respective set of measurements of radio frequency signals received by a radio frequency-receiving electrode from a radio frequency-transmitting electrode that transmitted radio frequency signals from within a body of a subject, and the selecting is based on comparison between the measurements to be analyzed and the sets of measurements used to construct the transformations.

There is provided, in accordance with some embodiments of the present disclosure, a system for estimating a position of a probe in a body cavity of a subject, wherein the probe comprises a radio frequency-receiving electrode and a radio frequency-transmitting electrode, the radio frequency-transmitting electrode being configured to transmit at a frequency that the radio frequency-receiving electrode is configured to receive, the system comprising: a processor configured to: obtain measurements of radio frequency signals received by the radio frequency-receiving electrode at radio frequencies transmitted from the radio frequency-transmitting electrode; and estimate a position of the probe with respect to the body cavity based on analysis of the measurements.

In some embodiments, the radio frequency-receiving electrode and the radio frequency-transmitting electrode are the same.

In some embodiments, the probe comprises a plurality of radio frequency-receiving electrodes, and the processor is further configured to estimate the position of the probe with respect to the body cavity based on measurements of radio frequency signals received by the plurality of radio frequency-receiving electrodes.

In some embodiments, the probe comprises a plurality of radio frequency-transmitting electrodes, each transmitting radio frequency signals at a respective frequency, wherein the radio frequency-receiving electrode is configured to receive radio frequency signals at the frequencies transmitted by all the radio frequency-transmitting-electrodes; and wherein the processor is further configured to estimate the position of the probe with respect to the body cavity based on measurements of radio frequency signals received by the receiving electrode.

In some embodiments, the probe comprises: a plurality of radio frequency-transmitting electrodes, each configured to transmit radio frequency signals at one or more respective frequencies, and a plurality of radio frequency-receiving electrodes, each configured to receive radio frequency signals at each of the frequencies the radio frequency-transmitting electrodes are configured to transmit; and the processor is configured to estimate the position of the probe with respect to the body cavity based on measurements of radio frequency signals received by the receiving electrodes.

In some embodiments, the processor is further configured to estimate the position of the probe by transforming the measurements to be analyzed using a transformation generated before the measurements to be analyzed was obtained.

In some embodiments, the processor is further configured to: select a transformation from among a plurality of transformations generated before the measurements to be analyzed were obtained; and transform the measurements to be analyzed using the selected transformation.

In some embodiments, each of the plurality of transformations is constructed using a respective set of measurements of radio frequency signals received by a radio frequency-receiving electrode from a radio frequency-transmitting electrode that transmitted radio frequency signals from within a body of a subject, and the processor is configured to select the transformation based on comparison between the measurements to be analyzed and the sets of measurements used to construct the transformations.

There is provided, in accordance with some embodiments of the present disclosure, a method of estimating a position of a first catheter in a first body cavity, the method comprising: receiving position-identifying data sets from electrodes of the first catheter; mapping the position-identifying data sets with a plurality of position-identifying data sets received from electrodes of a second catheter when the second catheter was in a plurality of different positions in a second body cavity; and estimating the position of the first catheter based on the mapping.

In some embodiments, the second catheter is the first catheter.

In some embodiments, the second body cavity is the first body cavity.

In some embodiments, the method further comprises: selecting a predetermined meta-set including the plurality of position-identifying data sets received from electrodes of the second catheter, the selecting being from among a plurality of predetermined meta-sets, each including a plurality of position-identifying data sets received from electrodes of a second catheter when the second catheter was in a plurality of different positions in a second body cavity; wherein the mapping comprises comparing the position-identifying data sets received from the electrodes of the first catheter with position-identifying data sets of the selected meta-set.

In some embodiments, selecting the meta-set comprises comparing between a first meta-set and a plurality of predetermined meta-sets, the first meta-set comprising a plurality of position-identifying data sets received from electrodes of the first catheter when the first catheter was in a plurality of different positions in the first body cavity.

There is provided, in accordance with some embodiments of the present disclosure, an apparatus for estimating a position of a first catheter in a first body cavity, the apparatus comprising: a digital memory storing a plurality of positions, each position stored in association with a respective identifier; and a processor configured to: receive measurements from electrodes of the first catheter when the first catheter is in the first body cavity; compare the measurements received with the identifiers stored on the digital memory; and estimate the position of the first catheter in the body cavity based on the comparison.

In some embodiments, each identifier comprises a set of measurements associated with a specified position, wherein: the set of measurements comprises measurements received from electrodes of a second catheter when the second catheter was in the specified position, and the specified position is a position in a body cavity.

In some embodiments, the identifiers are stored on the digital memory in training meta-sets, each training meta-set comprises a plurality of identifiers, and each identifier comprises a set of measurements associated with a different specified position.

In some embodiments, the processor is further configured to: receive a plurality of sets of measurements from electrodes of the first catheter when the first catheter is in a plurality of positions in the heart; and store each of the plurality of sets of measurements association with a respective position in which the first catheter was when the corresponding set of measurements was received, so as to store a test meta-set.

In some embodiments, the processor is further configured to select a training meta-set from a plurality of training meta-sets based on comparison of the training meta-sets with the test meta-set.

In some embodiments, the processor is configured to estimate the position of the first catheter based on comparison of measurements received from the first catheter when the first catheter is in the position to be estimated with measurements in the identifiers comprised in the selected training meta-set.

There is provided, in accordance with some embodiments of the present disclosure, a method of reconstructing a body cavity shape using intrabody positions of a probe having a plurality of electrodes, the method comprising: generating a plurality of electrical fields using the plurality of electrodes; measuring, at the intrabody positions and using the plurality of electrodes, a plurality of position-identifying data sets comprising a plurality of measurements of the plurality of electrical fields; and calculating a shape reconstructing the body cavity shape, based on the plurality of position-identifying data sets.

There is provided, in accordance with some embodiments of the present disclosure, a method of estimating a position of an intrabody probe having a plurality of electrodes, the method comprising: generating a plurality of different electrical fields using the plurality of electrodes; measuring, at an intrabody position and also using the plurality of electrodes, a position identifying data set comprising a plurality of measurements of the plurality of different electrical fields; and estimating position coordinates for the intrabody probe within an intrabody coordinate system, based on the position identifying data set.

According to some embodiments of the present disclosure, the estimating comprises determining the position coordinates based on a mapping between position coordinates in the intrabody coordinate system and position identifying data sets.

According to some embodiments of the present disclosure, the measuring detects differences among position identifying data sets measured by the plurality of electrodes at different intrabody positions due to changes in isopotential surface shapes of the plurality of different electrical fields as the intrabody probe moves.

According to some embodiments of the present disclosure, the measuring detects differences among position identifying data sets measured by the plurality of electrodes at different intrabody positions due to changes as the intrabody probe moves in the magnitudes of voltages established by controlled electrical currents.

According to some embodiments of the present disclosure, the position coordinates correspond to coordinates in a physical spatial coordinate system.

According to some embodiments of the present disclosure, the mapping is between position coordinates defined by anatomical data and position identifying data sets.

According to some embodiments of the present disclosure, the anatomical data comprise anatomical imaging data of a subject in which the intrabody probe is positioned.

According to some embodiments of the present disclosure, the mapping uses position coordinates defined with respect to measurements of crossing intrabody electrical fields generated by electrodes positioned away from the intrabody probe.

According to some embodiments of the present disclosure, the crossing intrabody electrical fields are generated from body surface electrodes.

According to some embodiments of the present disclosure, the plurality of different electrical fields comprises electrical fields generated at a plurality of frequencies.

According to some embodiments of the present disclosure, the frequencies of the plurality of frequencies are separated from each other by at least about 100 Hz.

According to some embodiments of the present disclosure, the plurality of different electrical fields is generated simultaneously.

According to some embodiments of the present disclosure, the plurality of different electrical fields is generated from at least two of the plurality of electrodes.

According to some embodiments of the present disclosure, the plurality of different electrical fields is generated from at least four of the plurality of electrodes.

According to some embodiments of the present disclosure, the plurality of different electrical fields is measured by at least two of the plurality of electrodes.

According to some embodiments of the present disclosure, the plurality of different electrical fields is sensed by at least four of the plurality of electrodes.

According to some embodiments of the present disclosure, the plurality of different electrical fields comprises at least 4 electrical fields, each sensed from two or more of the plurality of electrodes.

According to some embodiments of the present disclosure, the plurality of different electrical fields comprises at least 16 electrical fields, each sensed from four or more of the plurality of electrodes.

There is provided, in accordance with some embodiments of the present disclosure, a method of mapping an intrabody cavity for navigation by an intrabody probe having a plurality of electrodes, the method comprising: moving the intrabody probe to a plurality of intrabody positions while generating a plurality of different electrical fields using the plurality of electrodes; measuring position identifying data sets, wherein the position identifying data sets are measured at each of the plurality of positions and using the plurality of electrodes; associating each position identifying data set to the intrabody position at which it is measured to form a mapping; and storing the mapping for use in navigation of an intrabody probe.

There is provided, in accordance with some embodiments of the present disclosure, a system for intrabody navigation of an intrabody probe having a plurality of electrodes, comprising a processor configured to: receive a position identifying data set comprising a plurality of measurements of a plurality of different electrical fields generated using the plurality of electrodes, wherein the position identifying data set is measured using the plurality of electrodes; and estimate position coordinates for the intrabody probe within an intrabody coordinate system, based on the position identifying data set.

According to some embodiments of the present disclosure, the processor is configured to estimate the intrabody position based on a mapping between intrabody positions and position identifying data sets.

There is provided, in accordance with some embodiments of the present disclosure, a method of estimating a position of an intra-body probe comprising a radio frequency receiving electrode in a body cavity of a subject, the method comprising: analyzing data indicative of radio frequency signals received by the radio frequency receiving electrode from a radio frequency generating electrode that generates radio frequency signals from within the body of the subject; and estimating the position of the intra-body probe in respect to the body cavity based on results of the analyzing.

According to some embodiments of the present disclosure, the radio frequency receiving electrode receives the radio frequency signals when the radio frequency receiving electrode is in a heart chamber of the subject.

According to some embodiments of the present disclosure, the radio frequency generating electrode generates the radio frequency signals from within the heart chamber.

According to some embodiments of the present disclosure, the radio frequency receiving electrode and the radio frequency generating electrode are parts of the intra-body probe.

According to some embodiments of the present disclosure, the radio frequency receiving electrode and the radio frequency generating electrode are the same.

According to some embodiments of the present disclosure, the radio frequency generating electrode generates the radio frequency signals from within the coronary sinus of the heart of the subject.

According to some embodiments of the present disclosure, the analyzing comprises analyzing data indicative of radio frequency signals received by a plurality of radio frequency receiving electrodes, all forming parts of the intra-body probe; and the estimating comprises estimating the position of the intra-body probe in respect to the body cavity based on results of the analyzing.

According to some embodiments of the present disclosure, the analyzing comprises analyzing data indicative of radio frequency signals received from a plurality of radio frequency generating electrodes, each transmitting radio frequency signals at a respective frequency.

According to some embodiments of the present disclosure, the analyzing comprises transforming the data to be analyzed using a transformation generated before the data to be analyzed was obtained.

According to some embodiments of the present disclosure, the analyzing comprises: selecting a transformation from among a plurality of transformations generated before the data to be analyzed was obtained; and transforming the data to be analyzed using the selected transformation.

According to some embodiments of the present disclosure, each of the plurality of transformations is associated with a respective set of data indicative of radio frequency signals received by a receiving radio frequency electrode from a radio frequency generating electrode that transmitted radio frequency signals from within a body of a subject, and the selecting is based on comparison between the data to be analyzed and the sets of data associated with the transformations.

There is provided, in accordance with some embodiments of the present disclosure, a system for estimating a position of an intra-body probe in a body cavity of subject, wherein the intra-body probe comprises a radio frequency receiving electrode and a radio frequency generating electrode, the radio frequency generating electrode being configured to transmit at a frequency that the radio frequency receiving electrode is configured to receive, the system comprising: a processor configured to: obtain data indicative of radio frequency signals received by the radio frequency receiving electrode at radio frequencies transmitted from the radio frequency generating electrode; and estimate a position of the intra-body probe in respect to the body cavity based on analysis of the data obtained.

According to some embodiments of the present disclosure, the radio frequency receiving electrode and the radio frequency generating electrode are the same.

According to some embodiments of the present disclosure, the intra-body probe comprises a plurality of radio frequency receiving electrodes, and the processor is further configured to estimate the position of the intra-body probe in respect to the body cavity based on data indicative of radio frequency signals received by the plurality of radio frequency receiving electrodes.

According to some embodiments of the present disclosure, the intra-body probe comprises a plurality of radio frequency generating electrodes, each transmitting radio frequency signals at a respective frequency, wherein the radio frequency receiving electrode is configured to receive radio frequency signals at the frequencies transmitted by all the transmitting electrodes; and wherein the processor is further configured to estimate the position of the intra-body probe in respect to the body cavity based on data indicative of radio frequency signals received by the receiving electrode.

According to some embodiments of the present disclosure, the intra-body probe comprises: a plurality of radio frequency generating electrodes, each configured to transmit radio frequency signals at one or more respective frequencies, and a plurality of radio frequency receiving electrodes, each configured to receive radio frequency signals at each of the frequencies the transmitting electrodes are configured to transmit; and the processor is configured to estimate the position of the intra-body probe with respect to the body cavity based on data indicative of radio frequency signals received by the receiving electrodes.

According to some embodiments of the present disclosure, the processor is further configured to estimate the position of the intra-body probe by transforming the data to be analyzed using a transformation generated before the data to be analyzed was obtained.

According to some embodiments of the present disclosure, the processor is further configured to: select a transformation from among a plurality of transformations generated before the data to be analyzed was obtained; and transform the data to be analyzed using the selected transformation.

According to some embodiments of the present disclosure, each of the plurality of transformations is associated with a respective set of data indicative of radio frequency signals received by a receiving radio frequency electrode from a radio frequency generating electrode that transmitted radio frequency signals from within a body of a subject, and the processor is configured to select the transformation based on comparison between the data to be analyzed and the sets of data associated with the transformations.

There is provided, in accordance with some embodiments of the present disclosure, a method of estimating a position of a first catheter in a first body cavity, the method comprising: receiving position identifying data sets from electrodes of the first catheter; mapping the position identifying data sets with a plurality of position identifying data sets received from electrodes of a second catheter when the second catheter was in a plurality of different positions in a second body cavity; and estimating the position of the first catheter based on the on the mapping.

According to some embodiments of the present disclosure, the second catheter is the first catheter.

According to some embodiments of the present disclosure, the second body cavity is the first body cavity.

According to some embodiments of the present disclosure, the method further comprises: selecting a pre-stored meta-set including the plurality of position identifying data sets received from electrodes of the second catheter, the selecting being from among a plurality of pre-stored meta-sets, each including a plurality of position identifying data sets received from electrodes of a second catheter when the second catheter was in a plurality of different positions in a second body cavity; wherein the mapping comprises comparing the position identifying data sets received from the electrodes of the first catheter with position identifying data sets of the selected meta-set.

According to some embodiments of the present disclosure, selecting the meta-set comprises comparing between a first meta-set and a plurality of pre-stored meta-sets, the first meta-set comprising a plurality of position identifying data sets received from electrodes of the first catheter when the first catheter was in a plurality of different positions in the first body cavity.

There is provided, in accordance with some embodiments of the present disclosure, an apparatus for estimating a position of a first catheter in a first body cavity, the apparatus comprising: a digital memory storing a plurality of positions, each position stored in association with a respective identifier; and a digital processor configured to: receive measurements from electrodes of the first catheter when the first catheter is in the first body cavity; compare the measurements received with the identifiers stored on the digital memory; and estimate the position of the first catheter in the body cavity based on the comparison.

According to some embodiments of the present disclosure, each identifier comprises a set of measurements associated with a specified position, wherein: the set of measurements comprises measurements received from electrodes of a second catheter when the second catheter was in the specified position, and the specified position is a position in a body cavity.

According to some embodiments of the present disclosure, the identifiers are stored on the digital memory in training meta-sets, each training meta-set comprises a plurality of identifiers, and each identifier comprises a set of measurements associated with a different specified position.

According to some embodiments of the present disclosure, the digital processor is further configured to: receive a plurality of sets of measurements from electrodes of the first catheter when the first catheter is in a plurality of positions in the heart; and store each of the plurality of sets of measurements association with a respective position in which the first catheter was when the corresponding set of measurements was received, so as to store a test meta-set.

According to some embodiments of the present disclosure, the digital processor is further configured to select a training meta-set from a plurality of training meta-sets based on comparison of the training meta-sets with the test meta-set.

According to some embodiments of the present disclosure, the digital processor is configured to estimate the position of the first catheter based on comparison of measurements received from the first catheter when the first catheter is in the position to be estimated with measurements in the identifiers comprised in the selected training meta-set.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system" (e.g., a method may be implemented using "computer circuitry"). Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor (also referred to herein as a "digital processor", in reference to data processors which operate using groups of digital bits), such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well. Any of these implementations are referred to herein more generally as instances of computer circuitry.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device. A computer readable storage medium may also contain or store information for use by such a program, for example, data structured in the way it is recorded by the computer readable storage medium so that a computer program can access it as, for example, one or more tables, lists, arrays, data trees, and/or another data structure. Herein a computer readable storage medium which records data in a form retrievable as groups of digital bits is also referred to as a digital memory. It should be understood that a computer readable storage medium, in some embodiments, is optionally also used as a computer writable storage medium, in the case of a computer readable storage medium which is not read-only in nature, and/or in a read-only state.

Herein, a data processor is said to be "configured" to perform data processing actions insofar as it is coupled to a computer readable memory to receive instructions and/or data therefrom, process them, and/or store processing results in the same or another computer readable storage memory. The processing performed (optionally on the data) is specified by the instructions. The act of processing may be referred to additionally or alternatively by one or more other terms; for example: comparing, estimating, determining, calculating, identifying, associating, storing, analyzing, selecting, and/or transforming. For example, in some embodiments, a digital processor receives instructions and data from a digital memory, processes the data according to the instructions, and/or stores processing results in the digital memory. In some embodiments, "providing" processing results comprises one or more of transmitting, storing and/or presenting processing results. Presenting optionally comprises showing on a display, indicating by sound, printing on a printout, or otherwise giving results in a form accessible to human sensory capabilities. In some embodiments, digital memory may be part of the digital processor. In some embodiment, digital memory may be external to the digital processor.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1A:
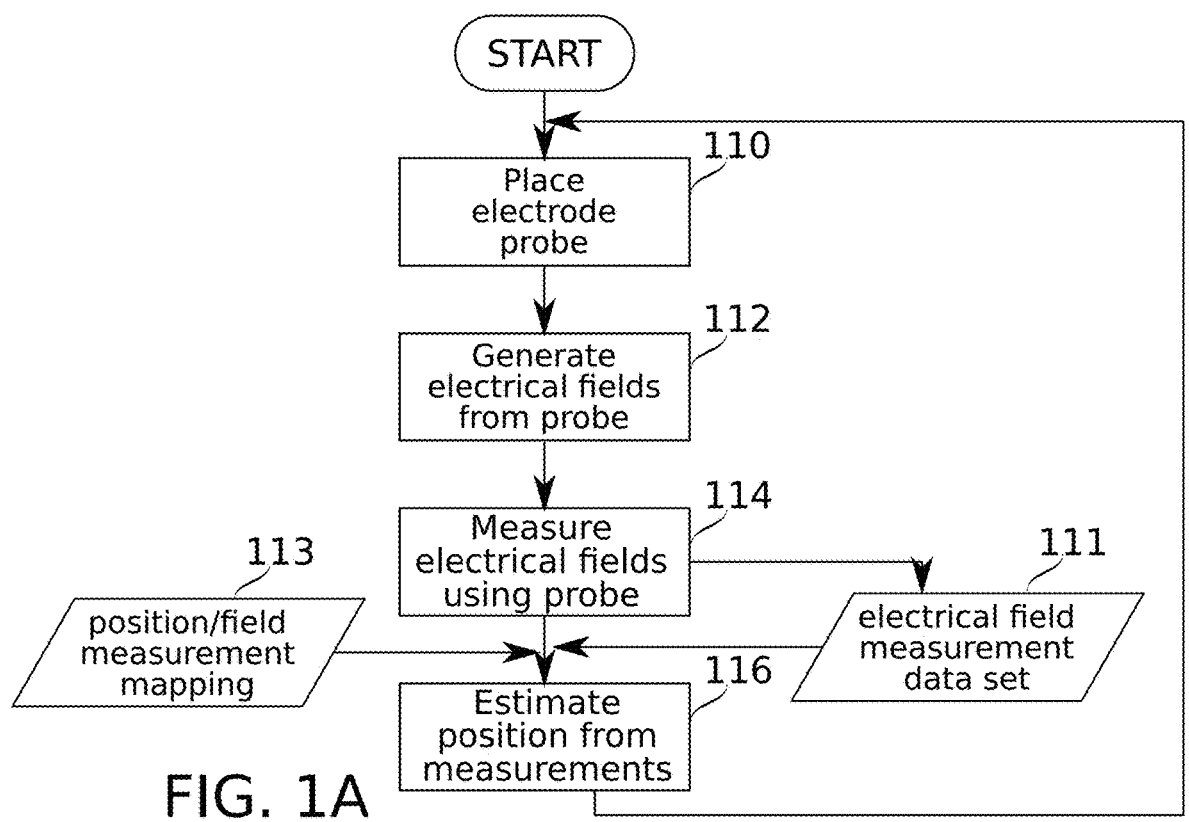
FIG. 1A is a flowchart of a method for finding an intrabody position of a probe based on measurement of electrical fields generated and measured from electrodes of the probe, according to some embodiments of the present disclosure.

The present invention, in some embodiments thereof, relates to the field of navigation of body cavities by intra-body probes, and more particularly, to determination of intra-body probe position, for example during navigation of body cavities.

Overview

A broad aspect of some embodiments of the present invention relates to tracking of a probe at intrabody positions using electrical fields. In some embodiments, the intrabody probe is a catheter probe (that is, a probe comprising sensors such as electrodes configured to perform measurements and borne on a distal portion of catheter). More particularly, in some embodiments, the catheter probe is an electrode-carrying portion of a catheter used to enter chambers of a subject's heart, e.g., for purposes of delivering treatment. In some embodiments, the treatment to be delivered is ablation (e.g., radio frequency ablation). Achieving successful treatment results, in some embodiments, relies on accurate positioning of the probe, for example, ablation success may rely on accurate positioning of the ablation catheter. In some embodiments, a probe is navigated to a heart or other body cavity for another purpose; for example, to map activity, measure tissue state, and/or deliver another treatment type.

Systems and methods have been described and in some cases are in use for providing intrabody probe spatial coordinate positioning information, including fluoroscopic, ultrasound, magnetic, and electroanatomical methods. Feedback to the user, enabling guided navigation and positioning of an intrabody probe, for example, a catheter probe, may comprise a visual representation of the space being navigated. For this and/or for other reasons, position information, at some stage of processing, is preferably expressed as position within a three-dimensional coordinate system, e.g., for generating a display image simulating a physical, three-dimensional space. Commensurate with this, probe position sensing and/or navigation systems that rely on some form of three dimensional sensing are in use.

As an example, some electroanatomical systems use impedance sensing of three or more crossing electrical fields, distinguishable by their frequencies, and which cross each other within an intrabody region to be navigated. In regions where the fields are approximately linear in physical space, and at least partially uncorrelated with each other in each of the three physical spatial dimensions, they can be treated as defining a three-dimensional impedance space. Optionally, the shape of that space is close enough to the shape of physical space that it can be displayed directly. Optionally, impedance space is transformed to more closely resemble the actual three-dimensional physical space by a suitable transformation.

Achieving characteristics of linearity and de-correlation of the electrical fields may place certain constraints on field-generating electrode positions. For some systems, the solution is to use body surface electrodes placed so that the fields they generate approximate, to the extent practical, orthogonal axes. The electrodes are far enough from each other that an approximately linear field region of useful size can be generated between them. Potential disadvantages of this include a reduction in sensitivity (e.g., since the voltage gradient, limited in total magnitude for safety reasons, is spread out over a long distance), complexity of setup (e.g., reproducible and/or cumbersome placement the body surface electrodes), and/or vulnerability to electrical instability and/or unpredictability (e.g., due to changes in electrical contact with the body surface, body movements, and/or inhomogeneities/variability in the large amount of "irrelevant" tissue that electrical fields need to penetrate before reaching the navigated region of interest).

An aspect of some embodiments of the present invention relates to the use of intrabody probe electrodes for generating, from within the body, electrical fields, and the use of those fields in intrabody probe navigation and/or mapping. Potentially, intrabody electrical field generation sites reduce some of the disadvantages of body surface electrodes. Measurements of electrical fields generated from positions nearby to target navigated/mapped body cavities are potentially less sensitive to variability in the electrical properties of body regions distant from the probe, and/or more sensitive to differences in position within the particular region of interest.

Potential relative loss of linearity and/or 3-D de-correlation in physical space from using nearby electrical field-generating electrodes is optionally mitigated by implementing collection of more electrical field information. Optionally, this comprises setting up a larger number of navigation fields, for example, 4 or more fields (e.g., 4-16 or more electrical fields; distinguished, for example, by frequency). In International Patent Application No. PCT IB2018/050289 entitled "CORONARY SINUS-BASED ELECTROMAGNETIC MAPPING", incorporated herein by reference in its entirety, catheter positioning (e.g., for navigation within chambers of the heart) is described that optionally provides a relatively large multiplicity of electrical fields generated from an electrode catheter placed within the coronary sinus, and/or placed in other intrabody locations close to the target intrabody navigation region from which the electrical fields are measured in order to obtain probe position information.

In some embodiments, a probe comprising electrodes used in generating the electrical fields used as position references is moved along with the sensing probe; and optionally is the same probe, as also described in the following aspect.

An aspect of some embodiments of the present invention relates to determination of the intrabody position of an intrabody probe, using electrical fields both generated and measured by a plurality of electrodes of that same intrabody probe (optionally, the same electrodes in each instance). In some embodiments, determinations of intrabody position are used to create a computed reconstruction of a body cavity shape, wherein the intrabody positions are determined using measurements of electrical fields both generated and measured by a plurality of electrodes of an intrabody probe positioned within the body cavity (optionally, the same electrodes in each instance).

Herein, such measurements are referred to as $V_{e-e}$ measurements or equivalently (in aggregate) as one or more "position-identifying data sets". "Position identifying data sets" optionally also include measurements made of electrical fields and/or radio frequency signals generated/transmitted from electrodes of one catheter, and measured/received from electrodes of another catheter. In some embodiments of the present invention, electrical field-generating electrodes and electrical field-measuring electrodes are placed not only intrabody, but also on the same probe (e.g., on the same catheter). Movement within a body lumen of a probe to which generating and measuring electrodes are mounted may induce changes in the electrode response to the electrical fields, e.g., in voltage measured at the electrodes. Such movement-induced changes may occur even where the positions (e.g., distances) of the generating and measuring electrodes in relation to each other are fixed. This may be due, for example, to differences in how electrical currents disperse as the probe is brought into different electrical environments. For example, dielectric properties of different tissues (e.g., cardiac muscle, lung, esophagus, vascular tissue, etc.) are different from each other, and/or different than blood, and therefore, for example, going toward or away from them may change measurements made from the electrodes.

Investigations by the inventors have indicated that differences among sets of $V_{e-e}$ measurements taken at different positions may be sufficiently distinct that they can be used as identifiers to "tag" different probe positions. In some embodiments, the tagging is performed with sufficient sampling density to allow mapping and/or navigation: using the measurement sites themselves, and/or using measurements interpolated to sites between measurement sites. Distinctness of identification (e.g., reduction of noise, increase in resolution, and/or reduction of ambiguity) is potentially increased by generating a relatively large number of distinguishable electrical fields, for example, 3-20 or more electrical fields. Measurement can also be made from a plurality of different electrodes; e.g., 4 or more probe electrodes each measuring 4 or more electrical fields potentially yields 16 or more different electrical measurements from a single probe position. In some embodiments, a probe comprising at least four electrodes is used to collect measurements; optionally, each electrode distinctly measures at least four different electrical fields.

An aspect of some embodiments of the present invention relates to the creation and use of mappings (predetermined associations) between measured positions in physical space, and electrical field measurements. Optionally, the electrical field measurements are $V_{e-e}$ measurements. Optionally, the electrical field measurements are another type of measurement, for example measurement from body surface electrodes, and/or electrodes of another intra-body probe. Creating such a mapping, in some embodiments, comprises use of a position sensing system (for example, an electroanatomical, magnetic, fluoroscopic, and/or ultrasound-based position sensing system) with an intrabody probe while making electrical field measurements with that probe. Position data from the position sensing system is associated with the electrical field measurements to generate the mapping.

Optionally, the mapping is, for example, implemented as a table, or converted to a mapping function (which may optionally be implemented as a neural net, computer code, coefficients of an analytical function, or another type of implementation). The mapping optionally maps sets of electrical field measurements (herein, a collection of such sets comprises a "meta-set") to physical spatial coordinates, and/or to quasi-spatial coordinates defined by axes of the measured parameters of the position measurement system.

Once a mapping is created, in some embodiments, it can optionally be used for positioning by making just the electrical field measurements, and looking up the position in the mapping. This can be performed using a first catheter for making the mapping, and a second catheter for the later positioning (optionally the first and second catheters are the same catheter).

In some embodiments, a mapping library is established, which incorporates mappings of meta-sets made for a plurality of previous subjects (optionally, previous patients). In some embodiments, mappings of the library comprise the meta-sets of data from which the mappings were determined.

For use with a current subject (further to the previous subjects, or a previous subject in a new session), a mapping may be selected from the library. Optionally, this selection is made on the basis of some initial $V_{e-e}$ measurement sets made with the current subject. The selection optionally is based on similarities of $V_{e-e}$ measurements from the current subject and of the previous subject (that is, a predetermined meta-set comprising $V_{e-e}$ measurements from a previous subject).

Optionally, the similarities are at identified landmarks (optionally, after application of a best-fit transformation method). Optionally, the selection of a mapping from the library is based on matching of the overall shape of $V_{e-e}$ point clouds (that is, the distribution in measurement space of $V_{e-e}$ measurement sets). Optionally or additionally, selection from a library is based on separately determined anatomical data. The anatomical data may be based, for example, on anatomical imaging data (CT or MRI imaging, for example) of the subject. Additionally or alternatively, the anatomical data are provided from an atlas (e.g., of anatomical imaging data from other subjects). Optionally, the anatomical data used is selected and/or modified based on additional data, for example, one or more subject medical history parameters such as age, sex, weight, and/or characteristics of subject disease. In some embodiments, shapes of body tissue defined by anatomical data (e.g., available from imaging and/or from another reconstruction) are used to define a reference shape, and positions of the $V_{e-e}$ point clouds are adjusted to match position coordinates of the reference shape.

In some embodiments, an additional transformation for matching of point clouds comprising $V_{e-e}$ measurement sets to one another is used. In some embodiments, a method of coherent point drift registration, or another registration type may be used for registering one point cloud to another.

In some embodiments of the invention, allowance is made for mappings that change over time, for example, due to the effects of treatments administered from a probe such as tissue ablation. In some embodiments, a change in electrical field measurements observed while a probe remains in place (and optionally if the change is associated with a treatment operation) is used to update a mapping of that position to the new electrical field measurements.

Definitions

Herein, the terms "map" and "mapping" (used as nouns) are used in reference to some embodiments to refer to predetermined associations (implemented, for example, using computer program code, tables, weighted neural network connections, coefficients of analytical functions, and/or other data structures) which allow conversion from an input of one data type to an output, optionally of another data type. Used as verbs, "map" and "mapping" refer to the construction of such data structures. In some embodiments of the invention, the types of the input data and the output data are different. For example, the two types may comprise distinct parameters and/or distinct numbers of parameters. In some embodiments, the input data type comprises a plurality of measurements by electrodes of an intrabody probe or probes, the measurements being of electrical fields also generated from those electrodes. In some embodiments, the output data type comprises a spatial position (e.g., a 3-D position in physical space). A mapping may comprise, for example, a look-up table and/or a function. Optionally, an input is equivalently said to be "converted", "mapped", or "transformed" into an output by use (equivalently, by "applying" or "application") of the mapping. A mapping may also "yield" an output from an input. Mappings are also referred to equivalently herein as "transformations". A mapping/transformation is "generated" upon the determination of its parameters and/or other data which describe how it may be applied to existing data (e.g., data based on which the transformation was generated), and optionally to further data.

More particularly, mappings used for some embodiments of the invention are optionally constructed empirically (empirical mapping) using associated measurements of the input data type and the output data type. In some embodiments described herein, association of input and output data comprises measurement of each under associating conditions; e.g., effectively simultaneously, and/or while a measuring probe remains substantially in a single position. In some embodiments, the associations of an empirical map are extended to cover non-measured data type values by interpolation between and/or extrapolation from actual associated measurements by any suitable method (e.g., spline fitting, linear quadratic or cubic interpolation, nearest neighbor interpolation, Lanczos resampling, etc.). Optionally or additionally, the associations of an empirical map are extended from empirical measurements based on theoretical considerations; for example, physical modeling of measured properties. In some embodiments, associated input and output data are used to determine a mapping function which transforms inputs (e.g., new measurements to which the mapping is applied) to exactly and/or approximately yield empirically determined associated outputs. Optionally, the mapping function yields an output when applied to an input which has not been seen yet, for example because it effectively interpolates/extrapolates output values, and/or by assigning the input to the output of the nearest-defined neighboring input.

Mappings are used, in some embodiments of the present invention, to convert a data type which is in some respect relatively convenient to obtain (e.g., convenient to measure) into a data type which is in some respect relatively more suitable for a particular use. In some embodiments, a mapping converts a multidimensional input data type (optionally, with more than 3, 4, 5, or 6 dimensions) into an output type which is used as a set of position coordinates, e.g., used for display, position finding, and/or navigation. The position coordinates optionally define positions of an object (for example, intrabody positions of a probe), and/or of one or more parts of an object (for example, a part of an intrabody probe such as its tip, an electrode, or another probe component) using a plurality of spatial dimensions (e.g., within a plane, along a surface, and/or in a 3-D region). The space used for the output data type is optionally a Euclidean space. Optionally, the position coordinates include coordinates describing an orientation of an object, e.g., the 3-D orientation of a probe positioned within a 3-D region. Position coordinates optionally include coordinates measuring time; for example linear time, and/or one or more phase parameters (e.g., heartbeat phase and/or respiratory phase).

Herein "position coordinates" refer to numbers used within a coordinate system; wherein the coordinate system uniquely identifies positions of different points on a manifold (e.g., three-dimensional manifolds corresponding to the three dimensions of physical space are referred to herein) by mutually distinct, ordered sets of position coordinates. Optionally, for each mapped value of the input data type, there is only one corresponding output data type value. In some embodiments, a mapping is one-to-many from input to output, and the resulting ambiguity is either tolerated, or resolved by some type of additional information. In some embodiments, the coordinate system used is explicitly related to physical space, e.g., such that Euclidean distances between points in the coordinate system are proportional to (or at least treated as being proportional to) physical distances they represent, and such that angles between points (that is, orientations of segments joining points) are (or at least treated as being) the same. Optionally, an additional transform is used in order to convert from a mapping output data type to a coordinate system which substantially resembles distances in physical space (e.g., neglecting residual error).

Optionally, the mapping itself incorporates the transform. In some embodiments, the coordinate system of the output data type is sufficiently close to representing physical space that it is used (e.g., displayed) "as if" it was a true spatial representation of distances.

For example, in some embodiments, coordinates of a three-dimensional space are defined by impedance values measured intrabody from time-varying electrical fields generated from body surface electrodes (or other electrodes located at positions away from the probe using the electrical fields for navigation and/or mapping) so that they cross each other in a region of interest for display, positioning and/or navigation. The three dimensions thus defined are not necessarily (and in some embodiments may never actually be) orthogonal and linear, but may be sufficiently close to be used as if they defined a physical space. Optionally, the three dimensions are transformed (e.g., scaled and/or rotated) to more accurately represent the relative angles and distances of physical space in the region of interest.

The term "intrabody coordinate system" as used herein, refers to a coordinate system which is used as a physical space coordinate system, e.g., for purposes of display, positioning, and/or navigation. The coordinate system is "intrabody", insofar as it refers to some particular physical region inside a subject's body, which in some embodiments comprises a lumen of an organ such as a heart. Herein, chambers of the heart (and more particularly, the left atrium) are used for purposes of describing examples, but it is to be understood that any other intrabody space navigable by a particular probe is optionally used; for example, a lumen of the gastrointestinal tract, a vascular lumen, a lumen of the urinary tract, a ventricle and/or canal of the central nervous system, and/or a space opened for surgical purposes. In some embodiments, estimating a position of an intrabody probe includes estimating position coordinates. Coordinates optionally include Cartesian axis coordinates for the intrabody probe within an intrabody coordinate system, for one or more parts of a positioned probe, and/or orientation coordinates for the intrabody probe or a part thereof.

Herein, reference is made to "measurements" of electrical fields. These measurements are optionally directly or indirectly of any parameter of the electrical field as detected from the position of the measuring device, for example voltage, current, and/or impedance. The electrical fields are time varying, in some embodiments; for example, time varying at frequencies of between about 10 kHz and 1 MHz. In some embodiments, electrical fields used are generated around a frequency of about 14 kHz. Electrical fields which are generated (and optionally measured) simultaneously are optionally separated from each other by any suitable frequency difference that allows them to be separately analyzed (even if measured simultaneously by the same electrode). In some embodiments, the frequency difference comprises steps of at least about 50 Hz, 100 Hz, 200 Hz, 250 Hz, 500 Hz, or another step size. Herein, the electrical fields generated and/or measured are equivalently referred to as generated, transmitted, measured, and/or received radio frequency signals (for example, signals at electromagnetic frequencies in the range of about 10 Hz up to about 1 MHz Accordingly, for example, an electrode (acting as a radio frequency antenna and/or receiver) may be referred to as a radio frequency-receiving electrode and/or a radio frequency-transmitting electrode. In some embodiments, one or more electrodes (e.g., electrodes of an electrode probe) are optionally configured to measure electrical fields, in addition to transmitting electrical fields. As the term is used herein, the term electrode may broadly refer to any structure from which electrical field may be transmitted (referred to herein as electrical field-generating electrodes and/or radio frequency-transmitting electrodes), and/or by which an electrical field and/or radio frequency may be received or measured (referred to herein as electrical field-measuring electrodes and/or radio frequency-receiving electrodes). The designations of electrodes and electrode types apply regardless of whether the structure was originally designed for purposes of transmitting, generating, and/or receiving or measuring electrical fields; and regardless of whether the structure serves any additional function (for example: one or more electrodes may additional serve for ablation, e.g., by RF ablation). Measured radio frequency signal may include any signal measured as result of transmission of a radio frequency signal by one or more radio frequency-transmitting electrodes. This includes measurement of an electrical field generated by the radio frequency signal transmission; for example: measurement of impedance, measurement of voltage, and/or another measurement, for example a measurement of a dielectric property.

Herein, where isopotential surfaces/lines are described (e.g., isopotential surfaces/lines of maximum and/or minimum potential reached during a frequency cycle), they are optionally understood alternatively as isoamplitude surfaces/lines (e.g., of radio frequency signals), or more generally as an isosurface of measured parameter. The "shape" of an isosurface of a parameter is the shape of a surface (in space, not necessarily a physical surface of an object) along which the parameter remains the same.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Use of Mappings to Find Probe Position from $V_{e-e}$ Measurements

Figure 1B:
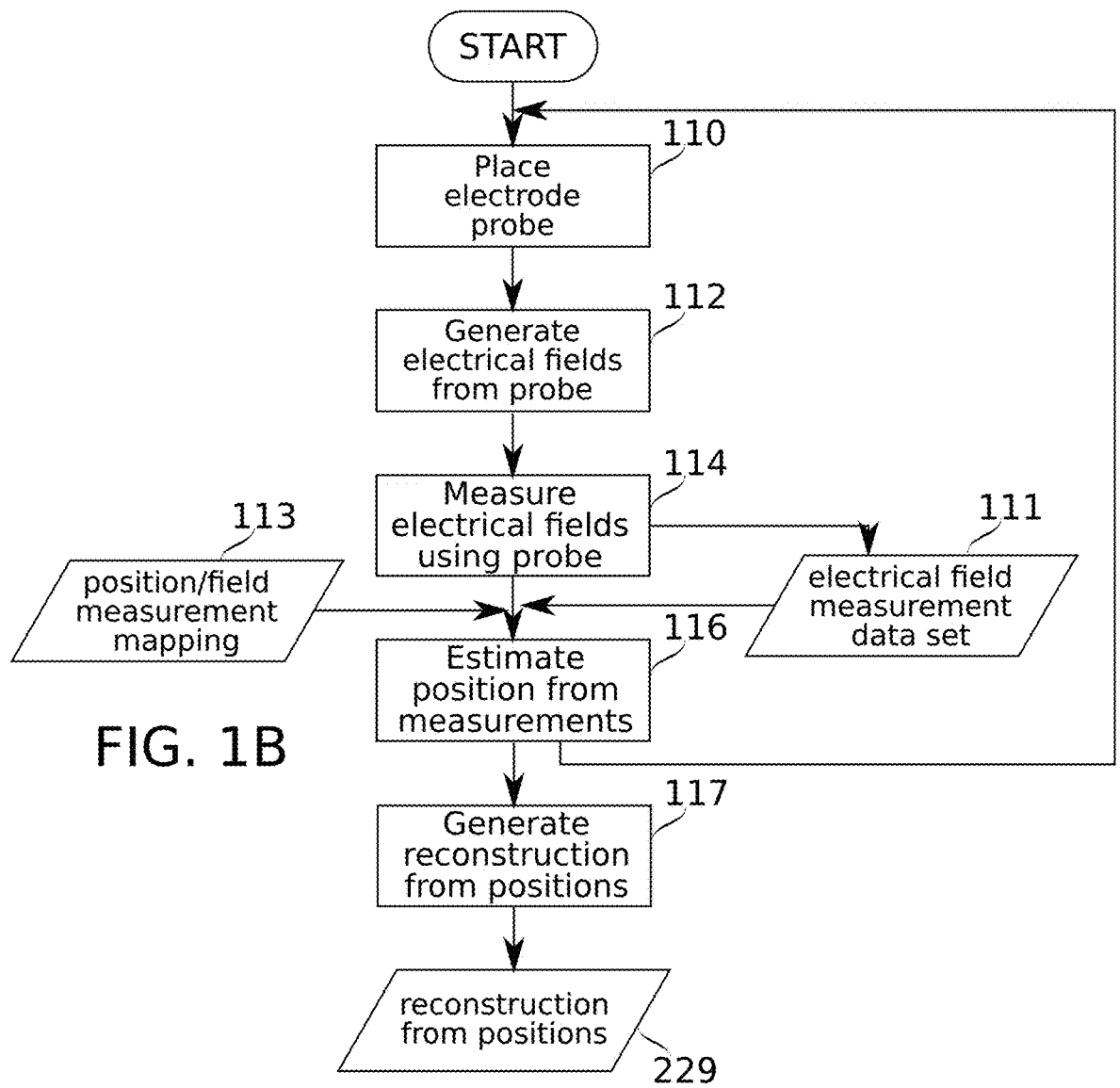
FIG. 1B is a flowchart of a method for finding an intrabody position of a probe based on measurement of electrical fields generated and measured from electrodes of the probe, and of calculating a reconstruction of a cavity within which the probe is moving, according to some embodiments of the present disclosure.

Reference is now made to FIG. 1A, which is a flowchart of a method for finding an intrabody position of a probe based on measurement of electrical fields generated and measured from electrodes of the probe, according to some embodiments of the present disclosure. Reference also made to FIG. 1B, which is a flowchart of a method for finding an intrabody position of a probe based on measurement of electrical fields generated and measured from electrodes of the probe, and of calculating a reconstruction of a cavity within which the probe is moving, according to some embodiments of the present disclosure.

Figure 3A:
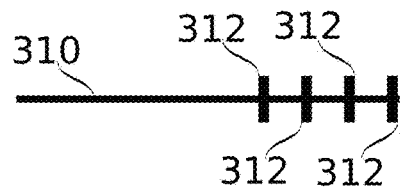
FIG. 3A schematically represents an electrode probe comprising electrodes, according to some embodiments of the present disclosure.

The flowcharts of both FIG. 1A and FIG. 1B start; and at block 110, in some embodiments, an electrode probe (e.g., electrode probe 310 of FIG. 3A, which is optionally a catheter probe) is placed within an intrabody space, for example, a lumen of a heart chamber. Brief reference is made to FIG. 3A, which schematically represents an electrode probe 310 comprising electrodes 312, according to some embodiments of the present disclosure. This highly schematic representation is shown magnified, to introduce its use in FIGS. 3C-4B. Four electrodes 312 are shown (four electrode catheter probes are available and commonly used in atrial fibrillation treatments, for example), but it is to be understood that any suitable number of electrodes are optionally present on probe 310, e.g., 2, 3, 4, 5, 6, 7, 8, 10, 20, 64, or another number of electrodes. Electrode configuration can be, for example, in a straight line, on a curved (e.g., "lasso") probe, and/or on a plurality of deployable struts (e.g., basket or umbrella electrode).

Returning to FIGS. 1A-1B: at block 112, in some embodiments, electrical fields are generated using one or more of the probe electrodes 312. In some embodiments (e.g., as described in relation to FIGS. 4A-4B), electrical fields are optionally generated between a plurality of electrodes 312, e.g., two electrodes electrically driven at the same frequency and an opposite phase. Alternatively or additionally, one or more of the electrical fields are driven from a single electrode 312, using an electrode placed elsewhere (e.g., body surface electrode 5 of FIG. 5) as a ground reference. In some embodiments, at least one electrical field is driven from each of electrodes 312, each at a different frequency (e.g., frequencies around about 14 kHz separated from each other by at least 100 Hz) relative to a ground reference. Optionally, any electrode 312 generates electrical fields at a plurality of frequencies, the electrical field at each frequency being itself generated by one or more of the electrodes 312. By using different combinations of electrodes and/or frequencies, the total number of distinguishable (that is, distinguishable by analysis of measurements made by a sensing electrode) electrical fields generated, in some embodiments is at least 4, 6, 8, 10, 12, 14, 16 or more electrical fields. In some embodiments, the fields are distinguished from one another by a frequency decomposition method such as a Fourier transform. In some embodiments, the fields are additionally or alternatively distinguished from one another by time multiplexing (i.e., different fields are activated at different times by cycling among them).

In some embodiments, a controlled electrical current is used in the generation of electrical fields from probe 310. Different dielectric environments conduct current with more or less impedance; e.g., so that a higher voltage is needed to pass the same current when impedance is also higher. This voltage change optionally is used in making the measurements, e.g., of block 114. In some embodiments, it is voltage which is controlled. Current required to maintain the voltage can then optionally be used as a measurement characteristic of the position of the generating electrode. Moreover, for positions away from the generating electrode (e.g., at other electrodes 312 of probe 310), different voltages may be measured in either controlled-current or controlled-voltage generating mode as the generated electrical fields are affected by movement of probe 310 into different dielectric environments.

At block 114, in some embodiments, the plurality of electrical fields generated from electrodes 312 of probe 310 is also measured using electrodes 312 of probe 310. For brevity (as mentioned already), such measurements are referred to herein as "$V_{e-e}$" measurements or as comprising a "position-identifying data set", meaning that electrodes of the same probe both generate the electrical field and measure electrical field properties provided as output (for example, electrical field measurement set 111, described below).

In some embodiments, the electrical field generation/measurement arrangement comprises each electrode 312 being driven to pass a known electrical current (e.g., from the electrode 312 to ground), while also measuring the resulting voltage at that same electrode 312. In some embodiments, electrodes 312 also make voltage measurements of local electrical impedance with respect to electrical fields generated by the other electrodes 312. For example, for four electrodes 312, each generating its own electrical field and measuring the fields of itself and all other electrodes 312, there may be a 4×4 measurement matrix (per measurement set obtained at a particular position) defined by the number of electrical fields generated x the number of measurement sites. Potentially, using more measurements to characterize a position helps to decrease noise and/or improve accuracy. It is to be understood that any other suitable arrangement (e.g., number) of fields and measurements may be used. For example, some of the fields are alternatively or optionally generated using body surface electrodes and/or electrodes on a separate intrabody probe, and optionally this generating is performed in combination with electrodes of the electrode probe that is also used for making measurements. The result of the measuring of block 114 is represented in FIGS. 1A-1B by electrical field measurement data set 111 (which may be stored, for example, as an array of measurement numbers, optionally referred to as a measurement vector).

At block 116, in some embodiments, a position of the electrode probe 310 is estimated, using the position-identifying data set, for example using electrical field measurement data set 111. In some embodiments, the position of the electrode probe 310 is estimated using a position/field measurement mapping 113. In some embodiments, estimating the position of the electrode probe includes estimating position coordinates for the intrabody probe within an intrabody coordinate system. Optionally, a position of the electrode probe 310 is estimated, using the measured and/or received position-identifying data set. The position/field measurement mapping 113 may comprise a function, table, or other data structure which allows look-up of a position based on the values of a position-identifying data set; for example: an electrical field measurement data set. Creation and/or selection of position/field measurement mapping 113 is detailed with respect to FIGS. 2A-2B, herein. An example of mapping creation and application is described with respect to FIG. 6, herein. In some embodiments, mapping 113 is generated before beginning operations of the flowchart of FIGS. 1A-1B (e.g., before beginning measuring). For example, the mapping is optionally generated for use as part of a library of mappings, from which a mapping is selected for use in a particular procedure.

In some embodiments, there is potentially an ambiguity in the mapping of a measurement data set to position. For example, a mapping function may provide several results. Optionally, such ambiguities are resolved by applying additional constraints. For example, the recent position history of the probe is used to see which of the positions outputted by the mapping function is more likely to have been reached when the measurements are taken, and position outputs which would move the probe in a sudden jump to a new location are ignored. For example, a limit is placed on the maximum change in position per millivolt of measured potential change (e.g., 2 mm/mV, 4 mm/mV, 8 mm/mV or another value).

Position estimation optionally continues by returning to block 110 of FIGS. 1A-1B.

Block 117 of FIG. 1B represents generation of a reconstruction (shown at block 229) from accumulated positions estimated at block 116 during iterations of the loop between blocks 110, 112, 114, and 116. As also explained in relation to FIG. 2A, herein, a mapping such as mapping 113 is optionally itself treated as a calculated "reconstruction," based, e.g., on the boundaries within which measurements used to create the mapping are positioned. In FIG. 1B, the basis of the reconstruction is not necessarily the mapping 113; rather, the positions estimated at block 117 are used.

Changes in Electrical Fields as a Function of Generating Electrode Position

Figure 4A:
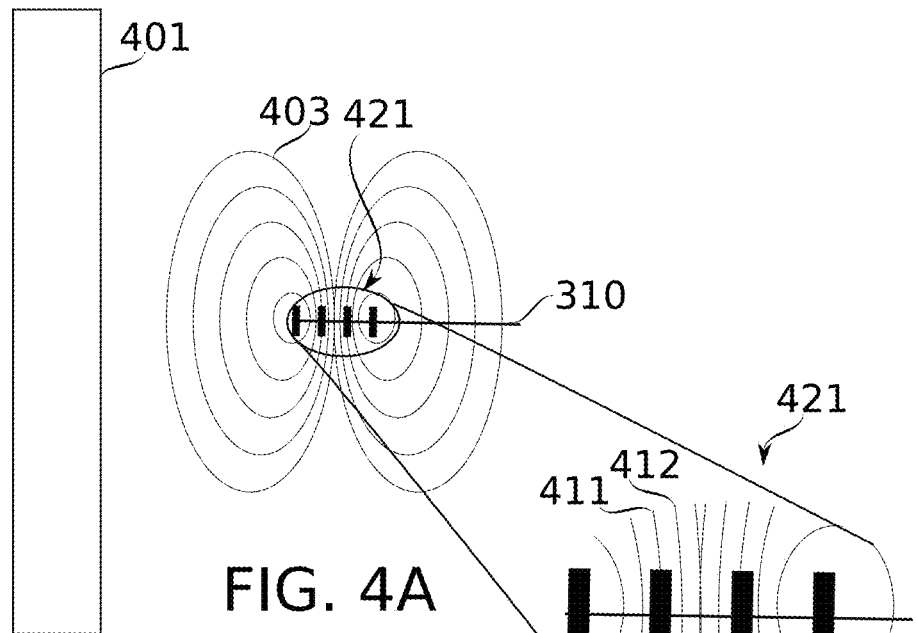
FIGS. 4A-4B schematically represent changes in the shape of an electrical field produced from electrodes of an intrabody probe as a result of movement to new surroundings, including changes in sensed electrical field parameters at the probe's electrodes according to some embodiments of the present disclosure.
Figure 4B:
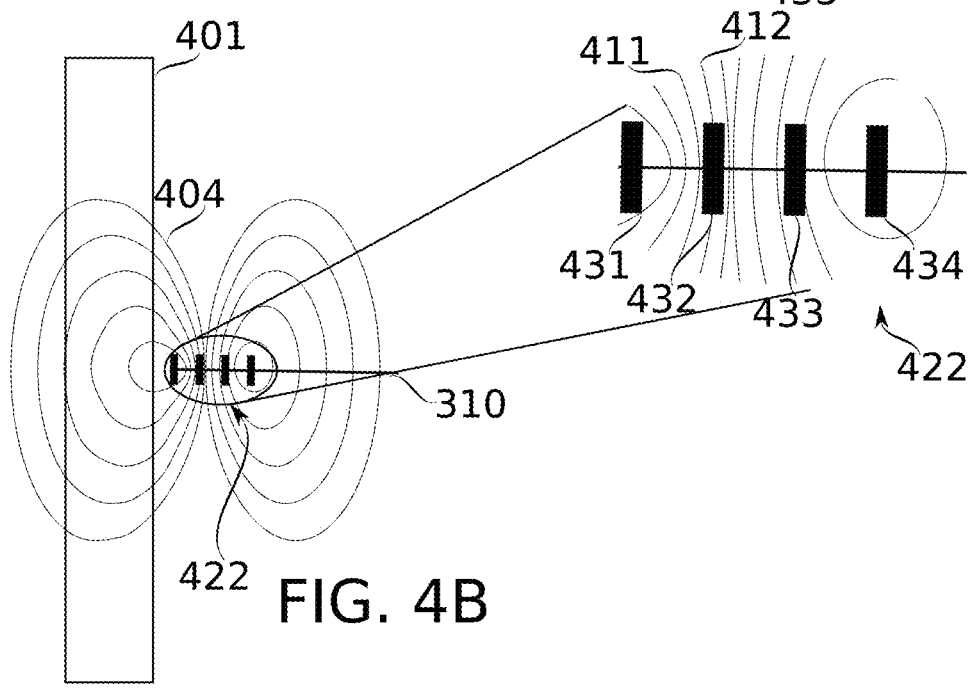

Reference is now made to FIGS. 4A-4B, which schematically represent changes in the shape of an electrical field from shape 403 shown in FIG. 4A, to shape 404 shown in FIG. 4B. The electrical field is produced from electrodes 431, 434 of an intrabody probe 310 as a result of movement to new surroundings, e.g., from a point away from wall 401 to a point near the wall. The changes in the field shape may be accompanied by changes in measured electrical field parameters at the probe's electrodes 432, 433 according to some embodiments of the present disclosure.

In FIG. 4A, generating electrodes 431 and 434 are shown, optionally operating at a shared frequency and at opposite phases to generate an alternating electrical field at radio frequencies. The field lines of electrical field 403 optionally represent positions of isopotential surfaces (within the plane of the drawing of FIG. 4A) at some phase of electrical field generation. Optionally, the lines represent isoamplitude surfaces of radio frequency signals generated by electrodes 431, 434. I In FIG. 4B, probe 310 has moved closer to tissue structure 401 (which may be, for example, a cardiac wall). Because the electrical properties (e.g., dielectric properties) of tissue structure 401 are different than the medium in which probe 310 is moving (blood, for example), the electrical field 404 generated by electrodes 431 and 434 changes its shape, compared to electrical field 403. One result of this shape change, in some embodiments, is that measurements from electrodes even on the probe 310 itself measure, e.g., different voltages as a function of generation phase.

This change is emphasized in the magnified regions 421 and 422 of FIGS. 4A and 4B, respectively. In FIG. 4A, an isopotential surface 411 (represented by a field line in the plane of the figure) is shown coinciding (e.g. at some phase of radio frequency field generation) with the position of electrode 432. Due to changes in the dielectric environment in FIG. 4B, the isopotential surface also changes relative to the generating electrodes, and now isopotential surface 412 coincides with the position of electrode 432. The different measurements, accordingly, are characteristic of different positions. With an appropriate selection of at least partially uncorrelated $V_{e-e}$ measurements, a measurement set is potentially identifying of different positions (that is, serves as an identifier). Optionally, the measurement set is uniquely identifying (within some margin of error) of a position; or if not, may be used as an identifier in conjunction with other information (such as recent position history of the probe) to unambiguously identify a position.

Figure 2A:
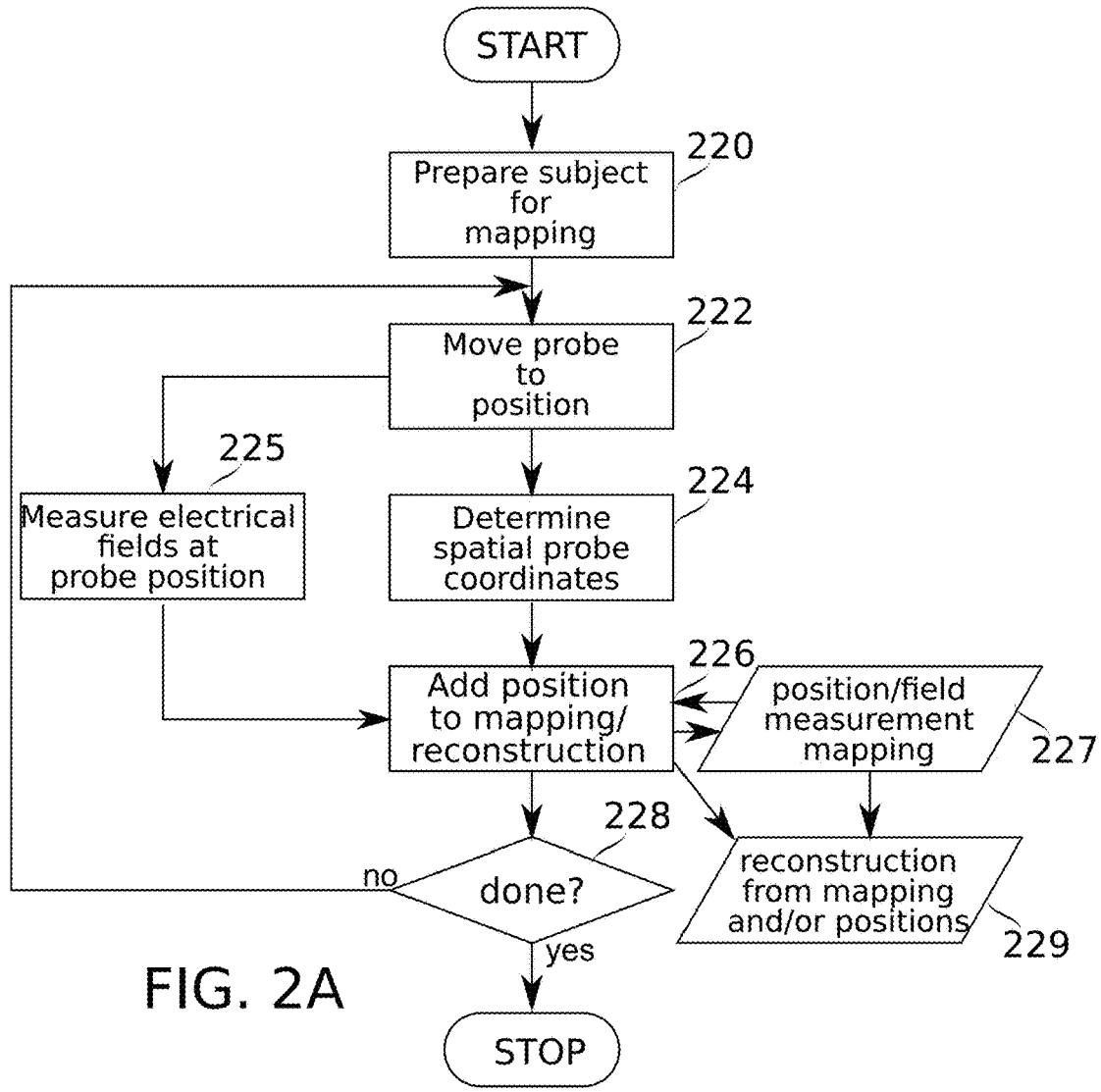
FIG. 2A is a flowchart of a method for mapping intrabody positions of a probe to measurements of electrical fields generated and sensed from electrodes of the probe, according to some embodiments of the present disclosure.

Building Mappings of Probe Position to $V_{e-e}$ Measurements
Method of Mapping Generation Reference is now made to FIG. 2A, which is a flowchart of a method for mapping intrabody positions of a probe to measurements of electrical fields generated and measured from electrodes of the probe, according to some embodiments of the present disclosure. In some embodiments, the mapping is used additionally or alternatively in producing a reconstruction of the shape of a body cavity in which the probe is moving.

At block 220, in some embodiments, a subject is prepared for mapping. This optionally includes preparation of the subject for application of a selected method of mapping, that allows an intrabody probe to be located within a spatial coordinate system; for example, electrical tracking using crossed electrical fields generated between body surface electrodes, magnetic tracking, imaging-based (e.g., ultrasound or fluoroscopic) tracking, etc. The example of FIG. 6, for example, uses tracking of probe position based on crossed, intrabody electrical fields generated from body surface electrodes. Preparing a subject at block 220 for mapping using such an example would comprise positioning of the body surface electrodes. In another example, International Patent Application No. PCT IB2018/050289 describes using intrabody electrodes placed in relatively fixed locations near a target lumen (e.g., on separate electrode catheters positioned in a coronary sinus, esophagus, and/or adjacent heart chamber in order to generate electrical fields used for electrical field-based position sensing of an electrode probe in a left atrium). Preparing a subject at block 220 in this case optionally comprises maneuvering electrical field generating probes into position.

At block 222, in some embodiments, an electrode probe (e.g., a catheter probe) is moved into a position within a body cavity which is to be mapped, for example a heart chamber such as a left atrium. The probe and probe placing are optionally as described with respect to the placing of block 110 of FIG. 1A.

At block 224, in some embodiments, spatial probe coordinates are determined, using the selected method of mapping into spatial coordinates (i.e., the method for which the subject was prepared, as mentioned at block 220). For example, in some embodiments, three crossed and frequency-distinguished electrical fields are imposed across the body cavity being navigated from body surface electrodes, and spatial coordinates are derived from suitably calibrated measurements of impedance for each electrical field at the position of the intrabody probe (roughly, the impedance measurement of each electrical field provides a coordinate corresponding to a spatial coordinate). Herein such measurements are also referred to as "pad measurements". Optionally, any other system capable of tracking a probe in three dimensions to yield spatial coordinates is used.

At block 225, in some embodiments, electrical fields generated from electrodes of the intrabody probe are measured by electrodes of the intrabody probe (optionally, the same electrodes). The generating and measuring are optionally performed as described for blocks 112 and 114 of FIG. 1A.

At block 226, in some embodiments, the measurements made at blocks 224 and 225 are added to a position/field measurement mapping 227 being extended and/or created. The mapping 227 is optionally a new mapping, or an existing mapping to which new measurements are being added. Optionally, mapping 227 is a mapping used as mapping 113 of FIG. 1A.

Adding the measurements to the mapping 227 optionally comprises associating the spatial coordinates of the probe measured at block 224 to the electrical field measurements of block 225 in the stored mapping 227. To a first approximation, the measurements from block 225 optionally are considered as being simply "tags", potentially having no systematic relationship to probe position in and of themselves. In this view, the mapping 227 simply associates tags to measured spatial positions provided by block 224. Such a mapping is optionally implemented simply as a look-up table.

In practice, however, the measurements of block 225 are based on continuously variable physical properties, so that they may be expected to show at least local spatial coherence, even if it is difficult to directly retrieve spatial coordinate positions from them. The property of spatial coherence means that measurements taken from probe positions near each other tend to be similar to one another. In some embodiments, this is used by converting (during measuring and/or after measuring is completed) the 1:1 mapping of $V_{e-e}$ measurements to position coordinates into a mapping function.

Block 229 represents a reconstruction computed from the position/filed measurement mapping and/or from measurements added to it from block 226 It should be noted that a sufficiently complete mapping 227, even as such, may also be considered as a basic type of reconstruction of a space such as a body cavity in which the intrabody probe is moving. This is true insofar as the directly mapped positions are bounded by the limits of the body cavity: the shape which those mapped positions define (e.g., considered as a cloud of measurement positions) "reconstructs" (by representation) the shape of the body cavity. In some embodiments, the mapping 227 is based (at least initially) on measurement data which provides incomplete coverage of the body cavity shape. Optionally, and even if the mapping 227 itself is left unchanged, addition of further measurements to reconstruction 229 improves coverage, to the point where the body cavity shape can be determined (again by defining the boundary between where the intrabody probe can and cannot go). However, in some preferred embodiments, measured positions allowing more complete reconstruction will also be used to provide a more refined position/field mapping 227, so that in practice the mapping 227 and at least a measurement position cloud-based reconstruction 229 are the same thing. This characterization of a cloud of measurement positions as a reconstruction also applies, in some embodiments, to accumulated position estimates of FIG. 1B, according to operations at block 117 to create a reconstruction from positions 229.

In some embodiments, computational methods are used to create a more developed type of reconstruction 229 based on the mapped positions added at block 226. For example, the cloud of measurement positions may be converted to a cavity shape by a "rolling ball" type method, wherein it is calculated to what positions a sphere of a certain size (or some point within the sphere) could reach if rolled over the cloud of measurement positions without intruding beyond any of the positions (alternatively, without intruding beyond some preset amount). This operation can convert discrete points of measurement positions into continuous surfaces, and the continuous surface may be used as a reconstruction of the body cavity shape. The surface can in turn be processed, e.g., into a polygon mesh representation suitable for rendering to a display image.

In another example of reconstruction: it may be apparent from the values and/or gradients of some of the measurements that they were made in contact with a wall of a body cavity. For example, locations near and/or in contact with body cavity walls may be notably distinct when approached and/or contacted by an electrode, due, e.g., to differences in conductivity (e.g., of cardiac tissue) compared to the medium (e.g., blood) existing within the body cavity lumen. In some embodiments, such measurements are assumed to define locations of the body cavity boundary (whether or not a full point cloud is available). Optionally those measurements are selected as a basis for calculating a reconstruction 229, for example using the rolling ball technique. Optionally, measurement positions estimated to be at the body cavity boundary are directly converted to a mesh reconstruction by connection of nearest neighbors, or another method. Such reconstruction methods are optionally implemented additionally or alternatively at block 117 of FIG. 1B using estimated positions separately from a mapping such as mapping 113 or 227.

Optionally, the mapping (table or function) converts $V_{e-e}$ measurements into pad measurements. A mapping of the pad measurements to physical spatial coordinates may allow converting the $V_{e-e}$ measurements to physical spatial coordinates in two steps: from $V_{e-e}$ measurements to pad measurements, and from pad measurements to physical spatial coordinates. Additionally or alternatively, pad measurements may be converted into physical spatial coordinates, e.g., by transforming a cloud of pad measurements into a cloud of measurements which fits within anatomical dimensions defined by imaging (e.g., CT), for example using a coherent point drift (CPD) method, such as is described in International Patent Application No. PCT IB2017/056616, entitled "SYSTEMS AND METHODS FOR REGISTRATION OF INTRA-BODY ELECTRICAL READINGS WITH A PRE-ACQUIRED THREE DIMENSIONAL IMAGE", the contents of which are incorporated herein by reference in their entirety.

Another method of converting electrical field measurements into dimensions which estimate anatomical (physical spatial) coordinates uses known distances between probe electrodes as a constraint, along with assumptions about the spatial coherence of pad measurements. Such methods are described, for example, in International Patent Application No. PCT IB2018/050192 entitled "SYSTEMS AND METHODS FOR RECONSTRUCTION OF INTRA-BODY ELECTRICAL READINGS TO ANATOMICAL STRUCTURE", the contents of which are incorporated herein by reference in their entirety. Additionally alternatively, mapping according to know distances is used as a method of determining spatial probe coordinates at block 224.

Several suitable methods known in the art may be applied to creating mapping functions. A simple example is a nearest-neighbor function, wherein sets of $V_{e-e}$ measurements are mapped to position coordinates through the defined set of $V_{e-e}$ measurements in the mapping that is closest (e.g., by Euclidean distance). In some embodiments, any suitable method of interpolation (linear, spline, etc.) is used to create a mapping function that allows assignment of position for sets of $V_{e-e}$ measurements that are not found in the original mapping data.

At block 228, in some embodiments, a determination is made as to whether the current mapping session is complete. If so, the flowchart ends. Otherwise, flow returns to block 222 for additional movement, electrical field generation/measurement, and mapping extension.

Once a mapping reaches a sufficient level of completeness, the method used for spatial probe position finding at block 224 is optionally halted. From that time, navigation optionally continues using the measurements of block 225 alone, based on the position/field measurement mapping 227. The mapping 227 can optionally be used from the beginning in a new (e.g. later) procedure (for example, used as mapping 113 of FIG. 1A), and optionally may form a basis for navigation in another patient whose anatomy sufficiently resembles that of the patient originally mapped. The mapping may also be added to by further measurements, e.g., by filling in measurement sets at positions between already mapped positions.

Schematic Illustration of Mapping

Figure 3B:
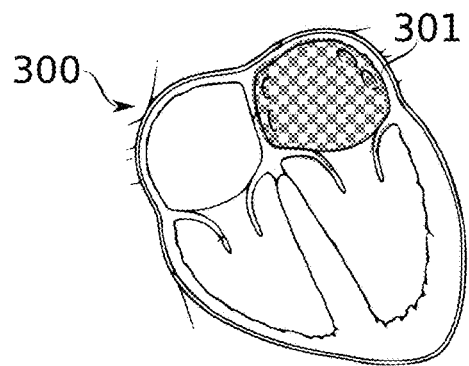
FIG. 3B schematically represents a cross-section of a heart.

Brief reference is now made to FIG. 3B, which schematically represents a cross-section of a heart 300. The shaded area represents the lumen of a left atrium 301, which is used as the intrabody region provided as an example in FIG. 3C, according to some embodiments of the present disclosure.

Figure 3C:
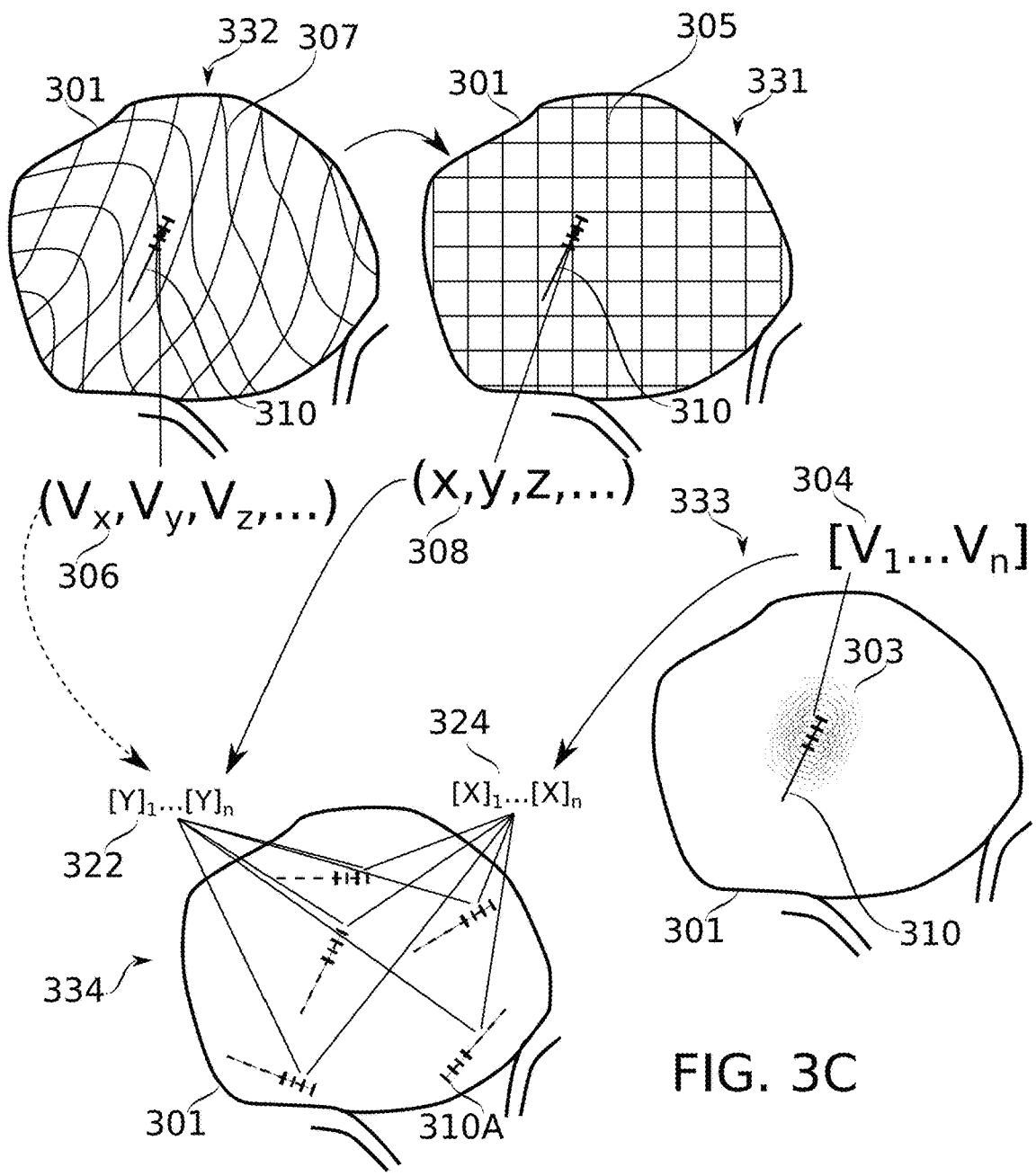
FIG. 3C schematically represents mapping from measurements of probe-generated and-measured electrical fields to physical spatial coordinates and/or quasi-spatial coordinates defined by measurements of crossed electrical fields, according to some embodiments of the present disclosure.

Reference is now made to FIG. 3C, which schematically represents mapping from measurements 304 of probe 310-generated and-measured electrical fields 303 to physical spatial coordinates 308 and/or quasi-spatial coordinates 306 defined by measurements of crossed electrical fields 307, according to some embodiments of the present disclosure.

Left atrium 301 cross-section 331 is marked with two dimensions a physical spatial coordinate system 305, including a probe 310 having physical spatial coordinates 308 (also referred to herein as "anatomical coordinates"); specified in the figure as Cartesian coordinates (x,y,z). The origin of a coordinate system is optionally a fixed origin, or defined relative to a potentially moving structure, such as a portion of a heart wall. Optionally, additional coordinates for fully specifying object position comprise specification of orientation and/or of additional spatial coordinates (e.g., specifying positions of different parts of the probe). Optionally, one or more physical coordinates expressing time is used, for example, heartbeat and/or respiratory phase. In some embodiments, the physical spatial coordinate system 305 is derived by calibrated transformation from a quasi-spatial coordinate system 307 (cross-section 332), for example, established by a probe position tracking system using measurements of crossed intrabody electrical fields generated from body surface electrodes (pad measurements). Coordinates 306 in the quasi-spatial coordinate system are optionally expressed as $(V_x, V_y, V_z \ldots )$. The quasi-spatial coordinate system 307 is optionally calibrated to physical spatial coordinates 305 (e.g., coordinates which directly correspond to physical distances and angles) by further processing, according to the position tracking method used.

Optionally, either type of coordinate system may be used as the basis of a probe position coordinate system, though there are potential advantages in use for coordinate systems which at least closely approximate the metrics of physical space. Measurement in either of physical spatial coordinate system 305 or quasi-spatial coordinate system 307 is optionally used, as the position output of, for example, block 225 of FIG. 2A, and/or of position measurement system 24 as described herein in relation to FIG. 5.

Cross-section 333 schematically indicates a different type of measurement, comprising a set of measurements 304 of probe 310-generated and-measured electrical fields 303. Set of measurements 304 has any suitable dimensionality (e.g., comprising 3, 4, 5, 8, 10, 12, 16, 20, 64, or another number of dimensions). Use of set of measurements 304 differs from the position coordinates 306, 308 of coordinate systems 307, 305 in that there is optionally no definite prior knowledge about how the different measurement values are distributed in space, except as externally established, for example, through a mapping. Even though there presumably is such a distribution (indeed, the process of mapping reveals this distribution), it may be too complex to be directly useful as an indication of physical position. For example, similar sets of measurements 304 (e.g., sets which are relatively "close" in Euclidean distance) may be recorded from widely separated physical regions of left atrium, while there may be more distant sets of measurements obtained from regions which are physically closer. Sets of measurements 304 may also comprise many more dimensions (measurements) than can be shown at once; e.g., latent spatial information is potentially distributed across more than three measurement dimensions.

Cross-section 334 indicates a portions of a mapping which associates positions 322 in one or more of the coordinate systems 307, 305 with sets of measurements 324, based on the two measurement vectors having been obtained under the same conditions; that is, while probe 310 remains in the same place. Several positions of probe 310 in cross-section 334 are indicated as probe positions 310A.

In some embodiments of the invention, the catheter itself comprises flexible and/or deployable parts, allowing electrodes to physically assume different relative position configurations. In some embodiments, creation of a mapping comprises reconfiguring the catheter into a plurality of different shapes (under control so that the shape is known, and/or under observation by a method allowing determination of the positions of electrodes in the changed shape), and obtaining sets of $V_{e-e}$ measurements 304 corresponding to different catheter configurations. Association between electrode positions and $V_{e-e}$ measurements comprises a "self-mapping" of the probe. Optionally, self-mapping is used to determine probe shape as it potentially changes over time (e.g., upon being pressed to heart wall). Optionally, probe shape is used as part of a mapping look-up.

Selecting Mappings from a Mapping Library and Preparing for Use

Figure 2B:
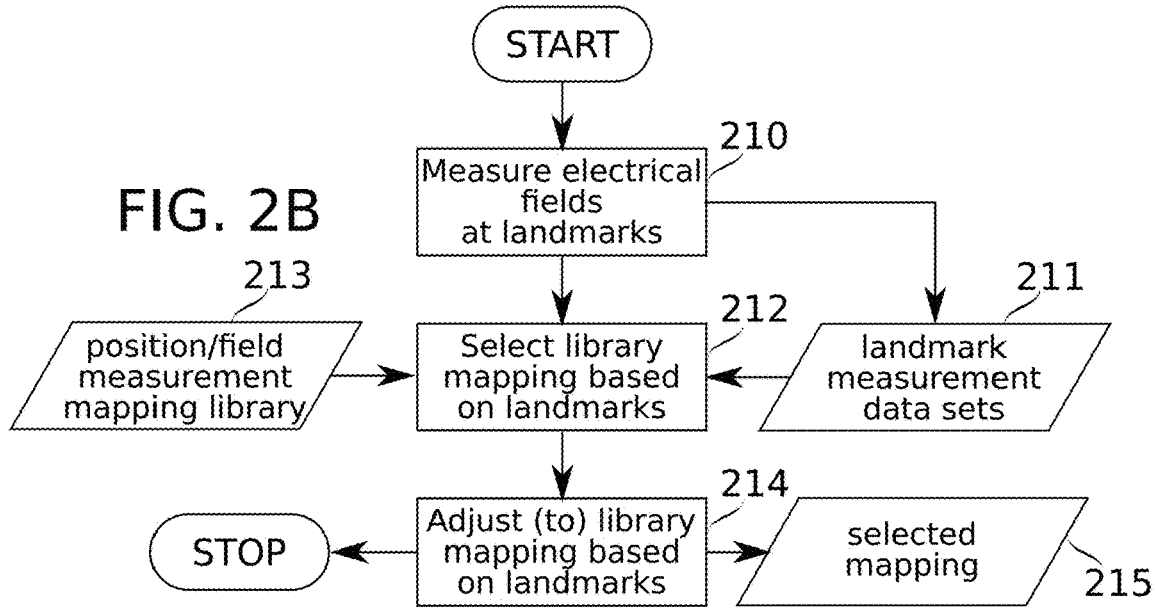
FIG. 2B is a flowchart of a method for selecting from a mapping library, and optionally adjusting, a mapping of intrabody positions of a probe to measurements of electrical fields generated and sensed from electrodes of the probe, according to some embodiments of the present disclosure.

Reference is now made to FIG. 2B, which is a flowchart of a method for selecting from a mapping library, a mapping of intrabody positions of a probe to measurements of electrical fields generated and measured from electrodes of the probe, according to some embodiments of the present disclosure. The method may also include adjusting the mapping.

Within a single subject, the mapping is potentially useful immediately upon being established; e.g., body surface pads could be disconnected from use, but navigation could continue as before, using established mappings between electrical $V_{e-e}$ measurements and probe positions. Even there, it is potentially useful to include a transformation stage in order to achieve improved results (this is described in relation to FIG. 6, herein).

In some embodiments, a plurality of mappings (comprising a "mapping library") is established for a relatively small number of subjects, and then applied for use in a larger subject population. Optionally, the number of mappings in the library comprises about 5, 10, 20, 50, 100, 150, or another number of mappings.

An optional use of a mapping library, in some embodiments of the present invention, is bypassing setup complexity and/or risk associated with methods for establishing physical spatial coordinate systems. Fluoroscopic methods, for example, are accompanied by radiation exposure risk. Methods using body surface electrodes not only entail spending time and other resources on positioning the electrodes, but also are potentially associated with risk of the body surface electrodes changing their contact properties over time (e.g., loosening or drying), which potentially produces degraded and/or misleading positioning results. A potential advantage of the present method over methods using intrabody electrodes placed on other electrode catheters may include, for example, saving time and other resources needed to position the other electrodes appropriately in the body of the subject.

The flowchart of FIG. 2B outlines a method for selecting a mapping from a mapping library, and optionally adjusting it for use with a particular subject and/or conversely, adjusting electrical field measurements from the subject for use with the selected mapping.

At block 210, in some embodiments, electrical fields are measured at landmark locations. In some embodiments, electrical fields generated from electrodes of a probe are measured using electrodes of the same probe at selected locations within a target body cavity of interest for navigation. Probe electrode and electrical field configurations are described, for example, in relation to FIG. 1A. In some embodiments, the selected locations comprise landmark location of the target body cavity and/or connected cavities. Landmarks may be any target which can be reliably and reproducibility identified and accessed by a probe (e.g., a catheter probe), optionally without use of a coordinate positioning system. For example, in the left atrium, landmarks optionally comprise roots of the pulmonary vein, the fossa ovalis of the septal wall, the mitral valve, etc. Optionally, landmarks are defined by a range of positions, for example, an electrode is guided to a pulmonary vein root and moved so that it crosses the vein root's full diameter in order to define its location. In some embodiments, landmarks are defined by positioning the probe at extremes of the range of available motion. The result of the measuring at block 210 is landmark measurement data sets 211. As described for other figures herein, the $V_{e-e}$ measurements associated with each landmark are multidimensional; comprising, for example, 3, 4, 6, 8, 10, 16, 20, 64, or another number of measurements.

At block 212, in some embodiments, a library mapping is selected from position/field measurement mapping library 213. In some embodiments, library mapping is selected based on landmark correspondences between the current subject's landmarks, and landmarks in mappings in the library. Landmarks are optionally specifically identified in mappings from the mapping library, to facilitate comparison. Optionally, the correspondence is based on some metric of similarity, e.g., Euclidean distances are calculated to corresponding $V_{e-e}$ measurements at landmarks identified in mappings of the library.

Optionally, finding of correspondence allows for some degree of transformation of $V_{e-e}$ measurements; e.g., a closest fit allowing for offsets, scaling, or another transformation. Transformation is optionally of just the $V_{e-e}$ landmarks.

In some embodiments, distances between electrodes used to make $V_{e-e}$ measurements are used in mapping library selection. For example, it is known from the mapping, in some embodiments, what the measurement difference should be between two measurement sites at some particular distance—and electrode-electrode distances are optionally known for the current subject, from the dimensions of the probe that carries them. Optionally, match checking to select a mapping includes verifying that this distance constraint is satisfied, and/or transforming to optimally satisfy it.

At block 214, in some embodiments, adjustment is optionally performed to improve the correspondence of the $V_{e-e}$ measurements from the subject, and the $V_{e-e}$ measurements of the selected mapping. In some embodiments, adjustment may be based on landmarks. The adjustment may comprise any suitable mathematical transform, for example, a linear transform.

Figure 6:
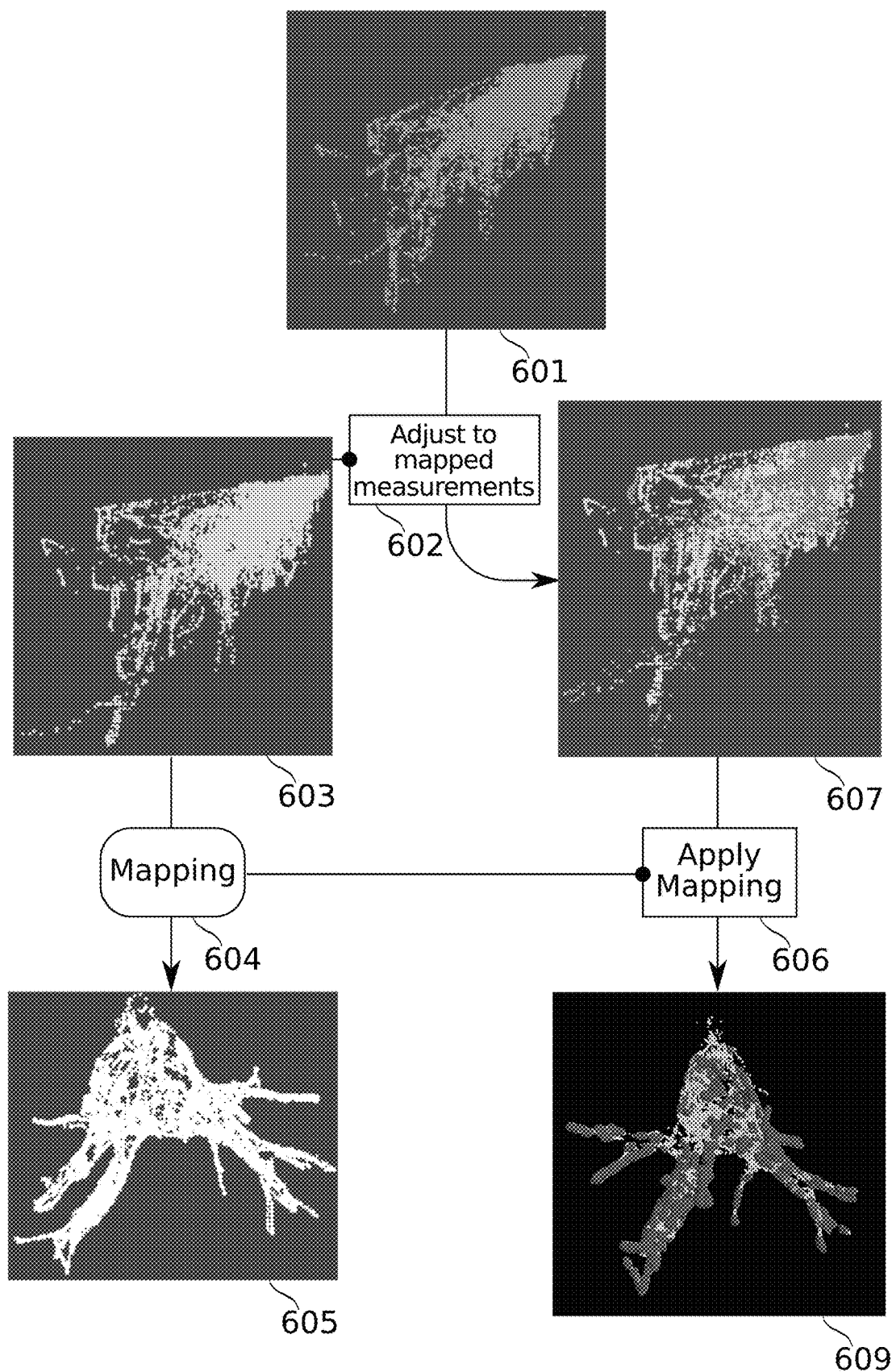
FIG. 6 provides an example of the creation and use of a mapping between position coordinate measurements and $V_{e-e}$ measurements, according to some embodiments of the present disclosure.

FIG. 2B is described in terms of $V_{e-e}$ measurements at landmarks. Another method of selecting a library mapping comprises taking enough $V_{e-e}$ measurements throughout a target region to define features of a point cloud of $V_{e-e}$ measurements, then selecting the library mapping whose own $V_{e-e}$ measurement point cloud most closely resembles the current subject's point cloud. Optionally, the library is selected after searching for an optimal transformation of a current $V_{e-e}$ measurement point cloud into a mapping's $V_{e-e}$ measurement point cloud, e.g., a CPD-type transformation). Examples of such point clouds using three measurement dimensions are shown in FIG. 6; any number of measurement dimensions is optionally used. FIG. 6 also describes use of coherent point drift (CPD) transform for improving agreement between $V_{e-e}$ measurements used to create a mapping, and $V_{e-e}$ measurements acquired later.

The selected mapping is made available in some embodiments as selected mapping 215, which optionally corresponds to the mapping used as position/field measurement mapping 113 of FIG. 1A. Optionally, moreover, new readings from the current subject are added into the source library mapping; for example added to the active mapping 227 as described in relation to FIG. 2A, and later back-transformed so that they can be integrated into the library mapping that originally provided mapping 227.

System for Creation, Selection and/or Use of Mappings

Figure 5:
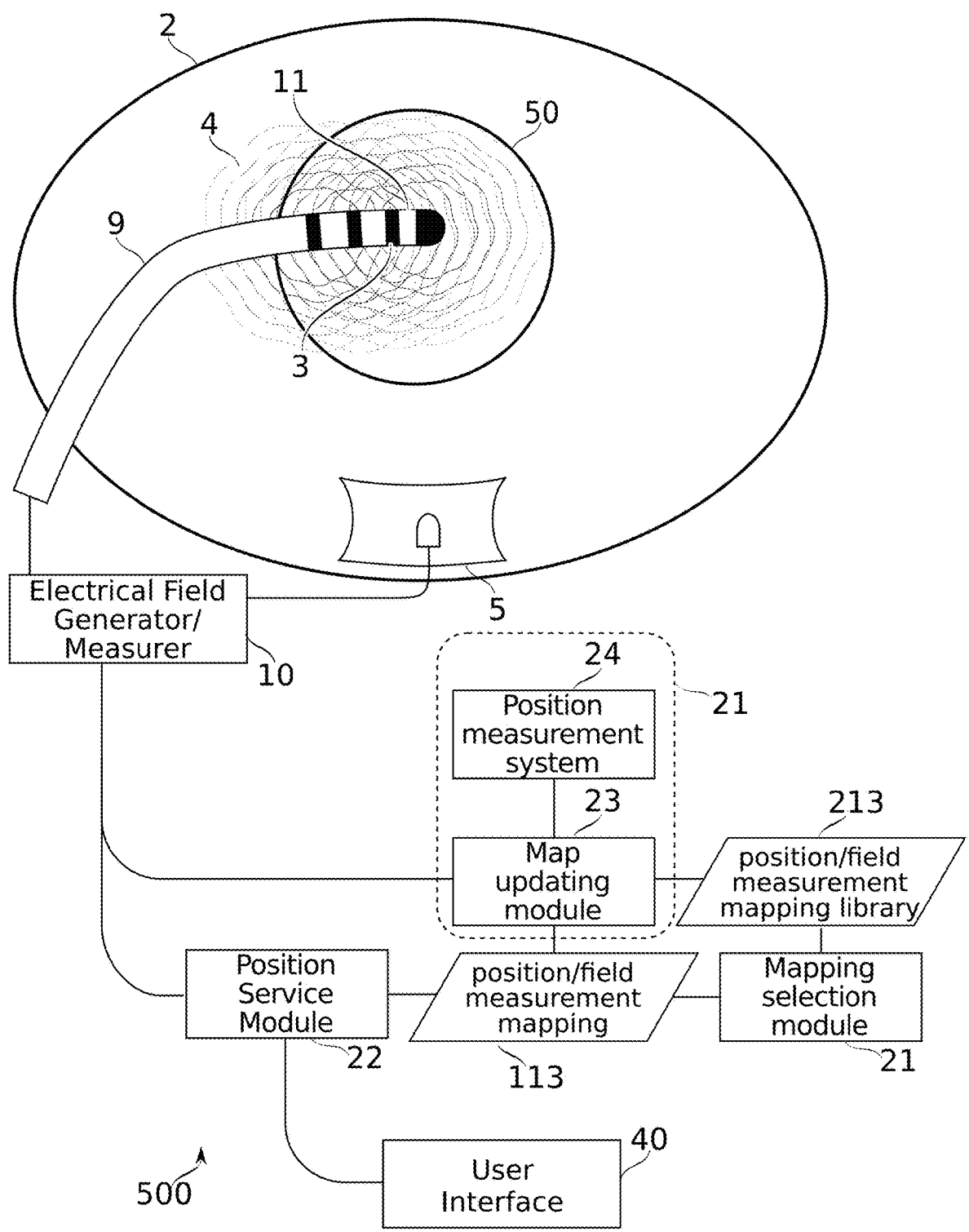
FIG. 5 schematically represents a system for making, selecting and/or using mappings between position coordinate measurements and $V_{e-e}$ measurements, according to some embodiments of the present disclosure.

Reference is now made to FIG. 5, which schematically represents a system 500 for making, selecting and/or using mappings between position coordinate measurements and $V_{e-e}$ measurements, according to some embodiments of the present disclosure.

A catheter 9 extends into body 2 to reach body cavity 50. Catheter probe 11 comprises electrodes 3, which optionally correspond, for example, to electrodes 312 (e.g., of FIG. 3A). The electrodes 3 are connected with electrical field generator/measurer 10, by means of which they are configured to emit electrical fields 4, and/or to measure the same electrical fields 4. Optionally, ground electrode 5 is also attached to electrical field generator/measurer 10. Measurements from the electrodes 3 of catheter probe 11 reach the position service module 22, which in some embodiments carries out the functions described in relation to block 116 of FIG. 1A, based on the received measurements and position/field measurement mapping 113. Optionally position estimates are provided to a user interface 40, allowing, for example, display of the estimated probe position. Optionally, there are also other modules which use the position information generated by position service module 22, for example, to plan, monitor, and/or predict the outcome of treatments (such as ablation treatments to treat atrial fibrillation) delivered using catheter probe 11.

Block 21 comprises an optional module for generating new mappings 113, including position system measurement 24 (for example, any position measurement system used to carry out the operations of block 224 of FIG. 2A), and map updating module 23 (configured, in some embodiments, to carry out functions of block 226 of FIG. 2A).

Optionally, produced mappings are provided as the active position/field measurement mapping 113, and/or added to a position/field measurement mapping library 213 (corresponding to block 213 of FIG. 2B). In some embodiments, optional mapping selection module 21 is configured to carry out the method of FIG. 2B, or another method of mapping selection and optionally transformation that yields a position/field measurement mapping 113 for use by position service module 22.

Example of Creation and Use of a Mapping

Reference is now made to FIG. 6, which provides an example of the creation and use of a mapping between position coordinate measurements and $V_{e-e}$ measurements, according to some embodiments of the present disclosure.

The light-shaded data points of plot 603 represent positions in a three dimensional space corresponding to three-measurement $V_{e-e}$ measurement sets (selected as the diagonal elements of the probe's self-measurement matrix), obtained for creation of a mapping (for example as described in relation to FIG. 2A) during movements of an electrode probe 11 in a test phantom representing a heart left atrium. The three axes of plot 603 correspond, in the example, to measurement magnitudes for each of three electrodes, each generating and measuring its own electrical field (more measurements could be taken with each measurement set, but three are used in the example for the sake of illustration).

Plot 605 shows position coordinates of probe 11 obtained during the measurement of the $V_{e-e}$ data points of plot 603. The positions shown in plot 605 were (obtained from measurements of body surface electrode-transmitted electrical fields, suitably transformed to physical spatial coordinates. Mapping 604 is a look-up function which associates each of the three-measurement $V_{e-e}$ sets of plot 603 to a corresponding physical spatial coordinate in plot 605. Mapping 604 is optionally index-to-index; that is, corresponding points in plots 603 and 605 share the same index.

After generation of mapping 604 was completed, another group of $V_{e-e}$ measurements was obtained, as shown in plot 601. Configuration of the measuring setup was allowed to change (e.g., the measurement apparatus was separately prepared for use in separate measuring sessions), so that the range of the measurements of plot 601 did not exactly reproduce the range of measurements shown in plot 603. At block 602, registration of the measurements of plot 601 to those of plot 603 was performed, using previously described mathematical techniques such as a multidimensional k-d tree algorithm and/or a CPD (coherent point drift) algorithm. The method used is similar to CPD algorithms described International Patent Application No. PCT IB2017/056616, entitled "SYSTEMS AND METHODS FOR REGISTRATION OF INTRA-BODY ELECTRICAL READINGS WITH A PRE-ACQUIRED THREE DIMENSIONAL IMAGE", the contents of which are incorporated herein by reference in their entirety. In that application registration is between pad measurements and physical (anatomical) coordinates; however, the same methods are optionally used, changed as necessary, for other types of "point cloud" registrations, such as $V_{e-e}$ to $V_{e-e}$ transformations.

The transformation allows data points of one point cloud to "drift" so that differences with another point cloud are minimized, while constraining points that begin as neighbors to drift with similar parameters so that they remain neighbors in the final result. The inventors have found that the registration is relatively insensitive to the parameters supplied to the transformation, so that it can be achieved without undue additional experimentation.

Plot 607 shows the lighter-shaded (yellow) $V_{e-e}$ measurements of plot 603, overlaid by the transformed, slightly darker shaded (green) $V_{e-e}$ measurements of plot 601.

In the final stage, the mapping 604 is applied at block 606 to the data of plot 607. The smaller, lighter-shaded points in plot 609 correspond to the $V_{e-e}$ measurements originally from plot 603, transformed into their corresponding positions in plot 605. The larger, darker-shaded points in plot 609 correspond to positions of the $V_{e-e}$ measurements originally from plot 601, after passing through the mapping function 604.

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A method of estimating an intrabody position of a probe having a plurality of electrodes, the method comprising:
    generating, from the intrabody position, a plurality of electrical fields using the plurality of electrodes;
    measuring, at the intrabody position and also using the plurality of electrodes, a position-identifying data set comprising a plurality of measurements of the plurality of electrical fields; and
    estimating a plurality of position coordinates defining the intrabody position within a spatial coordinate system, based on the position-identifying data set,
    wherein the estimating comprises determining the plurality of position coordinates defining the intrabody position based on a mapping between:
        additional position-identifying data sets comprising additional measurements of the plurality of electrical fields measured using the plurality of electrodes of the probe at a plurality of additional intrabody positions of the probe, and
        additional pluralities of position coordinates respectively defining the plurality of additional intrabody positions.

2. The method of claim 1, wherein measurements of the position-identifying data set measured by the plurality of electrodes are dependent on intrabody positioning of the probe, due to interactions of electrical fields generated by the plurality of electrodes with a local electrical environment dependent on intrabody position.

3. The method of claim 1, wherein values of the additional position-identifying data sets have a dependency on intrabody positioning of the probe, the dependency being due to changes in isopotential surface shapes of the plurality of electrical fields as the probe moves.

4. The method of claim 1, wherein values of the additional position-identifying data sets have a dependency on intrabody positioning of the probe, the dependency being due to changes, as the probe moves, in measured values of voltages established by controlled electrical currents provided by the plurality of electrodes.

5. The method of claim 1, wherein position coordinates of the plurality of position coordinates and the additional pluralities of position coordinates correspond to coordinates in the spatial coordinate system.

6. The method of claim 1, wherein the additional pluralities of position coordinates are defined by anatomical data, and the additional position-identifying data sets comprise measurements of the plurality of electrical fields.

7. The method of claim 6, wherein the anatomical data comprise anatomical imaging data of a subject in which the probe is positioned.

8. The method of claim 1, wherein the plurality of position coordinates is defined with respect to measurements of crossing intrabody electrical fields generated by electrodes additional to the plurality of electrodes and not disposed on the probe.

9. The method of claim 8, wherein the crossing intrabody electrical fields are generated from body surface electrodes.

10. The method of claim 1, wherein the plurality of electrical fields comprises electrical fields generated at a plurality of frequencies.

11. The method of claim 10, wherein the frequencies of the plurality of frequencies are separated from each other in steps of at least about 100 Hz.

12. The method of claim 10, wherein the fields of the plurality of electrical fields are generated simultaneously.

13. The method of claim 1, wherein the plurality of electrical fields is generated from at least two of the plurality of electrodes.

14. The method of claim 1, wherein the plurality of electrical fields is generated from at least four of the plurality of electrodes.

15. The method of claim 1, wherein the plurality of electrical fields is measured by at least two of the plurality of electrodes.

16. The method of claim 1, wherein the plurality of electrical fields is measured by at least four of the plurality of electrodes.

17. The method of claim 1, wherein the plurality of electrical fields comprises at least 4 electrical fields, distinguishable by at least one of the group consisting of current source, frequency, and time multiplexing; and each measured from two or more of the plurality of electrodes.

18. The method of claim 1, wherein the plurality of electrical fields comprises at least 16 electrical fields, distinguishable by at least one of the group consisting of current source, frequency, and time multiplexing; and each measured from four or more of the plurality of electrodes.

19. The method of claim 1, comprising using the estimated plurality of position coordinates to guide navigation of the probe within a body cavity.

20. The method of claim 1, comprising using the estimated plurality of position coordinates in reconstructing a shape of a body cavity.

21. A method of mapping a body cavity of a subject for navigation by a probe having a plurality of electrodes, the method comprising:
   receiving from the plurality of electrodes a position-identifying data set from each of a plurality of positions of the probe within the body cavity, each position-identifying data set comprising measurements, made by the plurality of electrodes, of a plurality of electrical fields, each electrical field being generated by one or more of the plurality of electrodes;
   associating each said position-identifying data set to the respective intrabody position at which it is measured to form a mapping, wherein the mapping is between:
      each respective position-identifying data set and position coordinates respectively defining the intrabody positions;
   storing the mapping for use in navigation of a probe;
   navigating the probe within the body cavity; and
   using the mapping to estimate an intrabody position of the probe, determined as a plurality of position coordinates within a spatial coordinate system, using at least one additional position-identifying data set comprising a plurality of measurements of the plurality of electrical fields measured using the plurality of electrodes as the probe is navigated within the body cavity and the plurality of electrodes generates the plurality of electrical fields.

22. The method of claim 21, wherein each of the plurality of electrical fields is generated by only one of the plurality of electrodes.

23. A method of estimating a position of a first catheter in a first body cavity, the method comprising:
   receiving position-Identifying data sets from a plurality of electrodes of the first catheter;
   mapping the position-identifying data sets with a plurality of additional position-identifying data sets received from a plurality of electrodes of a second catheter when the second catheter was in a plurality of additional intrabody positions in a second body cavity; and
   estimating the position of the first catheter as a plurality of position coordinates, the estimating being based on the mapping and on an additional mapping between:
      the plurality of additional position-Identifying data sets and additional pluralities of position coordinates respectively defining the plurality of additional intrabody positions of the second catheter,
   wherein each of the plurality of additional position-identifying data sets comprises additional measurements of a plurality of electrical fields, generated from and measured using the plurality of electrodes of the second catheter respectively at each of the plurality of additional intrabody positions of the second catheter.

24. The method of claim 23, wherein the second catheter is the first catheter.

25. The method of claim 23, wherein the second body cavity is the first body cavity.

26. The method of claim 23, further comprising:
   selecting a predetermined meta-set including the plurality of position-identifying data sets received from electrodes of the second catheter, said selecting being from among a plurality of predetermined meta-sets, each including a plurality of position-identifying data sets received from electrodes of a second catheter when the second catheter was in a plurality of different positions in a second body cavity;
   wherein the mapping comprises comparing the position-identifying data sets received from the electrodes of the first catheter with position-identifying data sets of the selected meta-set.

27. The method of claim 26, wherein selecting the meta-set comprises comparing between a first meta-set and a plurality of predetermined meta-sets, said first meta-set comprising a plurality of position-identifying data sets received from electrodes of the first catheter when the first catheter was in a plurality of different positions in the first body cavity.

28. A method of estimating an intrabody position of a probe having a plurality of electrodes, the method comprising:
   generating, from the intrabody position, a plurality of electrical fields using the plurality of electrodes;
   measuring, at the intrabody position and also using the plurality of electrodes, a position-identifying data set comprising a plurality of measurements of the plurality of electrical fields; and
   estimating a plurality of position coordinates defining the intrabody position within a spatial coordinate system, based on the position-identifying data set;
   wherein the position-identifying data set has a dependency on intrabody positioning of the probe, the dependency being due to changes in isopotential surface shapes of the plurality of electrical fields as the probe moves.

29. A method of estimating an intrabody position of a probe having a plurality of electrodes, the method comprising:
   generating, from the intrabody position, a plurality of electrical fields using the plurality of electrodes;
   measuring, at the intrabody position and also using the plurality of electrodes, a position-identifying data set comprising a plurality of measurements of the plurality of electrical fields; and
   estimating a plurality of position coordinates defining the intrabody position within a spatial coordinate system, based on the measurements of the plurality of electrical fields in the position-identifying data set, without use of anatomical imaging data, including without use of anatomical imaging data from other subjects.

30. The method of claim 29, wherein measurements of the position-identifying data set measured by the plurality of electrodes are dependent on intrabody positioning of the probe, due to interactions of electrical fields generated by the plurality of electrodes with a local electrical environment dependent on intrabody position.

31. The method of claim 29, wherein values of the additional position-identifying data sets have a dependency on intrabody positioning of the probe, the dependency being due to changes in isopotential surface shapes of the plurality of electrical fields as the probe moves.

32. The method of claim 29, wherein values of the additional position-identifying data sets have a dependency on intrabody positioning of the probe, the dependency being due to changes, as the probe moves, in measured values of voltages established by controlled electrical currents provided by the plurality of electrodes.

33. The method of claim 29, wherein position coordinates of the plurality of position coordinates and the additional pluralities of position coordinates correspond to coordinates in the spatial coordinate system.

34. The method of claim 29, wherein the plurality of position coordinates is defined with respect to measurements of crossing intrabody electrical fields generated by electrodes additional to the plurality of electrodes and not disposed on the probe.

* * * * *